US012345590B1

(12) United States Patent
Smith

(10) Patent No.: US 12,345,590 B1
(45) Date of Patent: Jul. 1, 2025

(54) MEASUREMENT INSTRUMENT FOR MEASURING FORCE AND DISPLACEMENT DATA FROM A SURGICAL SPREADER

(71) Applicant: Briant Smith, Sonoma, CA (US)

(72) Inventor: Briant Smith, Sonoma, CA (US)

( * ) Notice: Subject to any disclaimer, the term of this patent is extended or adjusted under 35 U.S.C. 154(b) by 0 days.

(21) Appl. No.: 19/086,216

(22) Filed: Mar. 21, 2025

Related U.S. Application Data

(60) Provisional application No. 63/572,293, filed on Mar. 31, 2024.

(51) Int. Cl.
*G01L 5/00* (2006.01)
*A61B 17/02* (2006.01)
*A61B 90/00* (2016.01)
*G01L 1/22* (2006.01)

(52) U.S. Cl.
CPC .......... *G01L 5/0038* (2013.01); *A61B 17/025* (2013.01); *A61B 90/06* (2016.02); *G01L 1/22* (2013.01); *A61B 2017/0268* (2013.01); *A61B 2090/064* (2016.02)

(58) Field of Classification Search
CPC ......... G01L 5/0038; G01L 1/22; A61B 90/06; A61B 2090/064; A61B 17/025; A61B 2017/0268
See application file for complete search history.

(56) References Cited

U.S. PATENT DOCUMENTS

| | | | | |
|---|---|---|---|---|
| 1,985,108 | A * | 12/1934 | Rush | A61B 17/8866 606/86 R |
| 4,898,161 | A * | 2/1990 | Grundei | A61B 17/2812 81/356 |
| 8,777,953 | B1 * | 7/2014 | Khalili | A61B 17/7086 606/86 A |
| 9,233,275 | B2 * | 1/2016 | Gatherer | A63B 21/4001 |
| 11,666,318 | B2 * | 6/2023 | Otto | G01L 5/0057 606/90 |
| 12,042,179 | B2 * | 7/2024 | Rubod | A61B 17/44 |
| 12,059,167 | B2 * | 8/2024 | Vogtherr | A61B 17/28 |
| 2010/0030223 | A1 * | 2/2010 | Keller | A61B 17/1767 606/99 |
| 2022/0096248 | A1 * | 3/2022 | Dressler | A61F 2/4657 |

FOREIGN PATENT DOCUMENTS

CN 111902096 A * 11/2020
DE 102010015890 A1 * 9/2011

* cited by examiner

*Primary Examiner* — Octavia Hollington
(74) *Attorney, Agent, or Firm* — Adam Warwick Bell; Phillip Wagner

(57) ABSTRACT

A measurement instrument configured for removable attachment to the two opposing handgrips of a surgical spreader includes a force transducer and a displacement transducer arranged to measure, store, and transmit mechanical forces acting on or imposed by the surgical spreader and relative spatial displacements of the jaws and/or handgrips of the surgical spreader. The measurement instrument enables accurate, precise measurements of force and displacement to be made with many different types of manually-operated surgical spreaders. A measurement instrument may exchange force and displacement measurements with another measurement instrument to aid a surgeon performing an assessment of joint anatomy and/or prosthetic joint component size, adjustment, and placement.

14 Claims, 13 Drawing Sheets

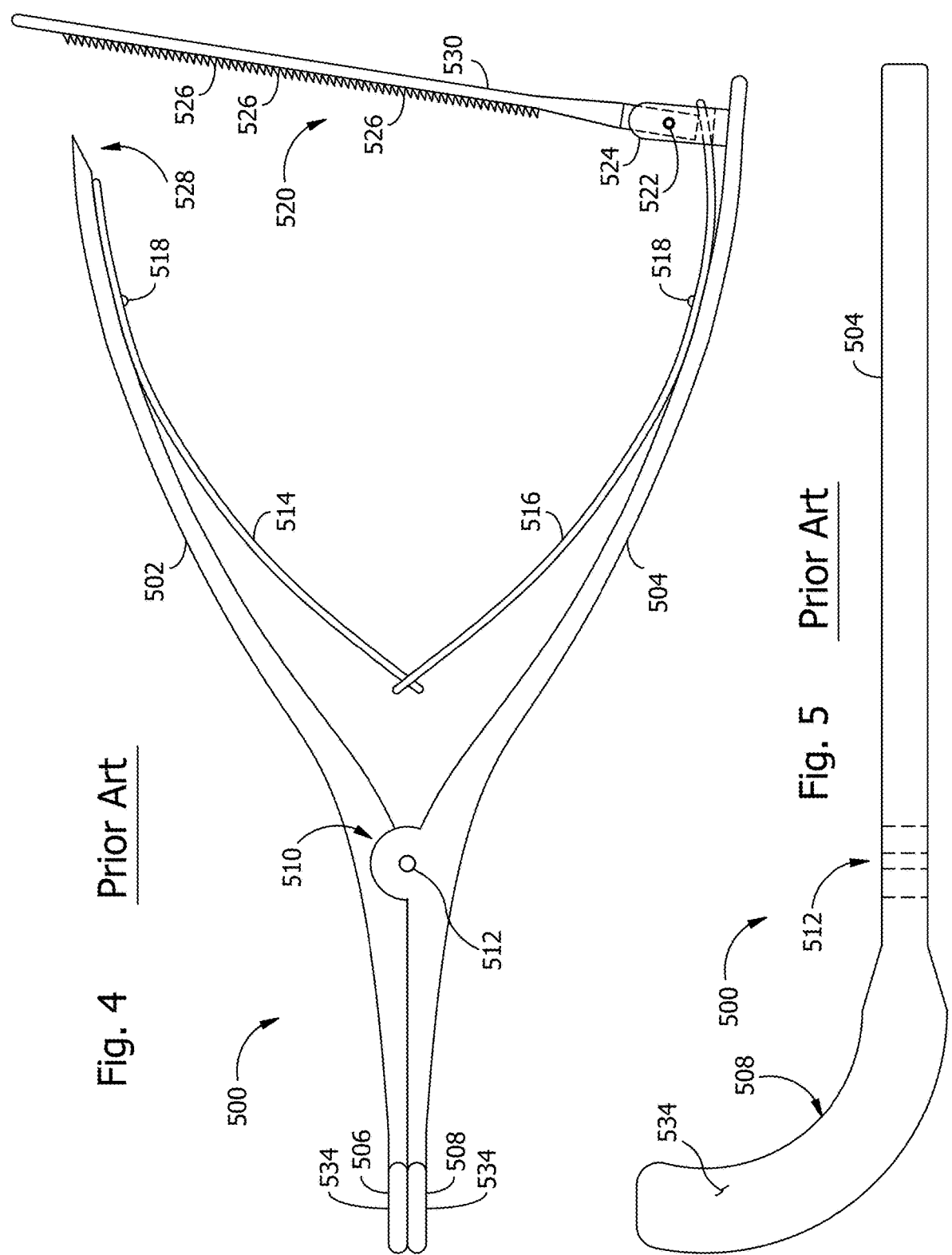

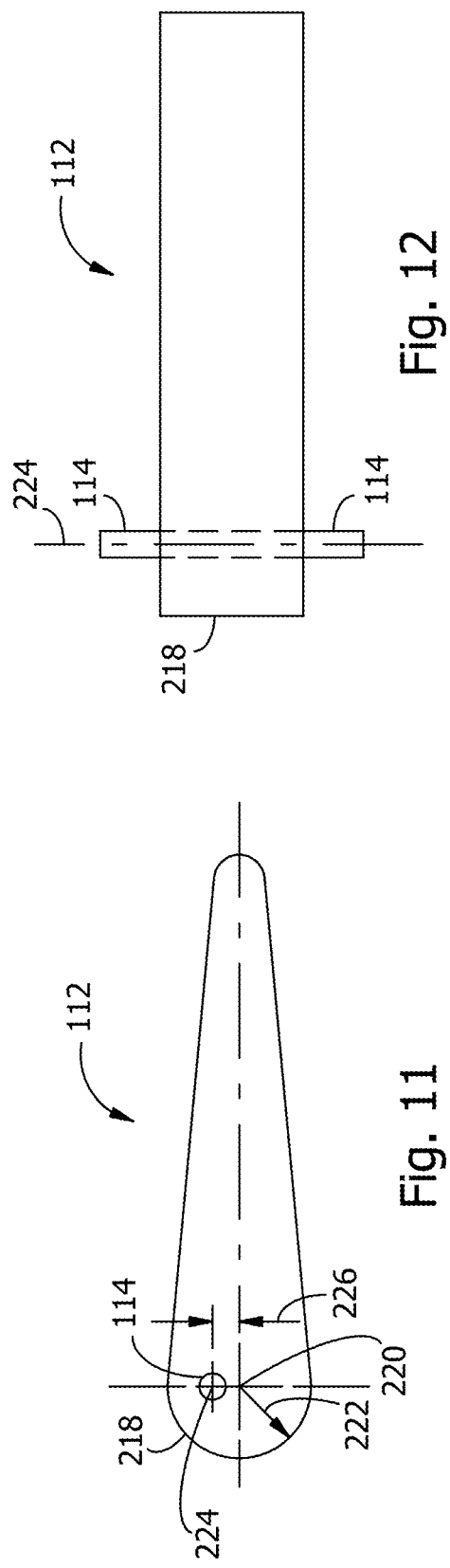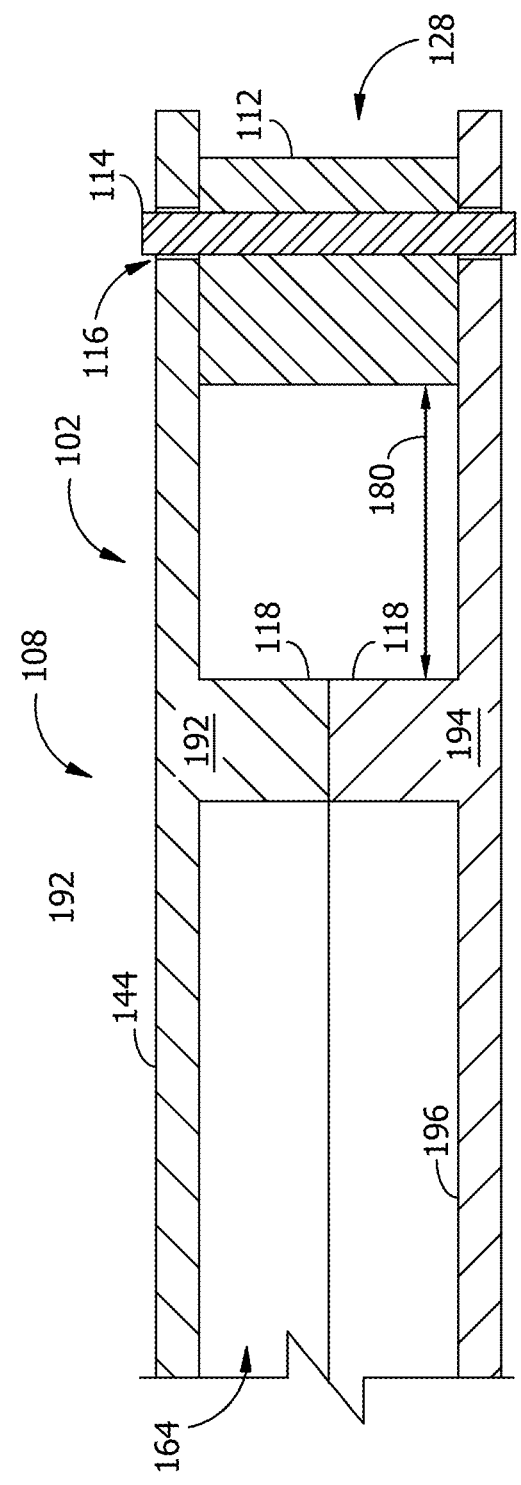

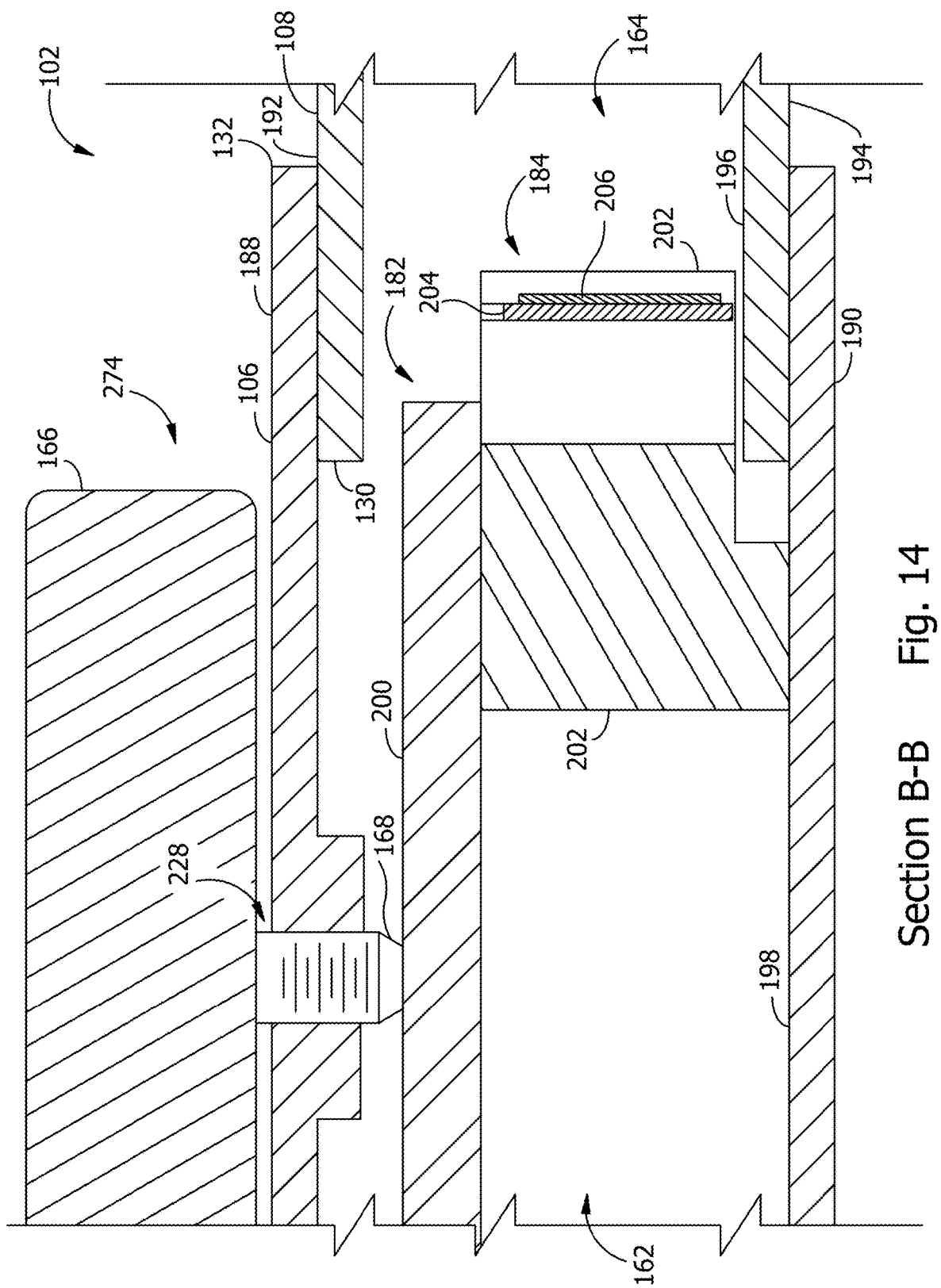
Section B-B    Fig. 14

MEASUREMENT INSTRUMENT FOR MEASURING FORCE AND DISPLACEMENT DATA FROM A SURGICAL SPREADER

RELATIONSHIP TO OTHER APPLICATIONS

This application claims priority and benefit from U.S. provisional application No. 63/572,293, filed 1 Apr. 2024.

GOVERNMENT SUPPORT

None

FIELD OF THE INVENTION

The field of the invention relates to spreader devices for performing surgical procedures on skeletal joints.

BACKGROUND

Some manually-operated surgical instruments include two jaws and two handgrips attached to one another at a rotatable coupling referred to as a fulcrum. Each jaw is attached to or integrally formed at an end of a handgrip with the fulcrum intervening between the jaw and handgrip. Examples of a rotatable coupling include a pin passing through apertures formed in both rotating parts, a cylindrical projection from one part fitting into an aperture in the other part, and a box joint. Examples of manually-operated surgical instruments with rotatably coupled jaws and handgrips include, but are not limited to, surgical spreaders, femoral tibial spreaders, balancing tensioners, and retractors. The jaws may be referred to as blades, even though the jaws or blades may be intended for pushing, separating, or grasping rather than cutting. For discussion purposes herein, all such devices are referred to as surgical spreaders. A surgical spreader may be configured such that moving the spreader handgrips toward one another causes the spreader jaws to move apart from one another, and moving the spreader handgrips away from one another causes the spreader jaws to move toward one another, although other arrangements are available.

A surgical spreader may include a locking mechanism for retaining the spreader handgrips and/or spreader jaws at selected separation distances from one another. Some locking mechanisms are indexed and others are continuously variable. An example of an indexed locking mechanism includes a clamp bar having an end rotatably attached to one of the spreader handgrips with the clamp bar formed with indexing features such as grooves, teeth, or ridges shaped to engage with an end of the opposing spreader handgrip. When engaged with the end of the opposing spreader handgrip, the clamp bar is capable of holding the spreader jaws and spreader handgrips at a separation distance selected from discrete, predetermined spatial positions determined by the shape and placement of the indexing features. An indexed locking mechanism having a clamp bar formed in this manner may be referred to as a ratchet mechanism.

Unlike an indexed locking mechanism, a continuously variable locking mechanism enables a separation distance between the spreader jaws and/or spreader handgrips to be set to any value within the movement range of the locking mechanism. An example of a continuously variable locking mechanism includes a threaded rod having an end rotatably attached to a first spreader handgrip, an aperture formed in the opposing second spreader handgrip for admittance of the threaded rod, and a threaded handgrip locking knob engaged with the threaded rod with the handgrip locking knob positionable to press against the second spreader handgrip. Another example of a continuously variable locking mechanism includes a smooth bar or rod having an end rotatably coupled to a spreader handgrip and a spring-loaded latch attached to the opposing spreader handgrip, with the latch configured to slide along the bar until the latch is engaged to hold the bar and spreader handgrips stationary relative to one another. Whether equipped with an indexed or a continuously variable locking mechanism, a surgical spreader may further include one or more handgrip springs positioned to urge the spreader handgrips apart from one another and press the spreader handgrips against the locking mechanism.

Some previously available surgical spreaders include printed or engraved indicia relating to a separation distance of the spreader jaws and/or spreader handgrips, but those surgical spreaders may not be configured to measure and/or indicate a compression force exerted by a person's hand on the spreader handgrips, a compression force exerted by anatomical parts of a knee joint or joint prosthetic components on the surgical spreader jaws, forces exerted against the spreader jaws after a person releases the spreader handgrips, and/or a separation distance of the spreader jaws at smaller increments than the intervals between indexing features in a locking mechanism.

BRIEF DESCRIPTION OF THE DRAWINGS

FIG. 4 illustrates an example prior art surgical spreader having two spreader handgrips and two spreader jaws rotatably coupled to one another at a fulcrum, representing an example of a surgical spreader with an indexed locking mechanism and two handgrip springs, and further representing one of many alternative surgical spreader configurations that may be used with the disclosed measurement instrument embodiments.

FIG. 5 is a side view of the example surgical spreader of FIG. 4.

FIG. 11 is a view toward a front side of an example handgrip clamp lever.

FIG. 12 is a side view of the example handgrip clamp lever of FIG. 11.

FIG. 13 shows a partial cross-sectional view A-A of an example engagement between a handgrip clamp lever with the inner housing front cover and the inner housing back cover of the telescoping enclosure. A location and viewing direction for cross-sectional view A-A is marked with section line A-A in FIG. 3.

FIG. 14 is a partial cross-sectional view B-B of examples of the force measurement actuator, the force transducer, the outer housing, and the inner housing included with some embodiments of the measurement instrument. A location and viewing direction for cross-sectional view B-B is marked with section line B-B in FIG. 9.

SUMMARY OF THE INVENTION

Figure 1:
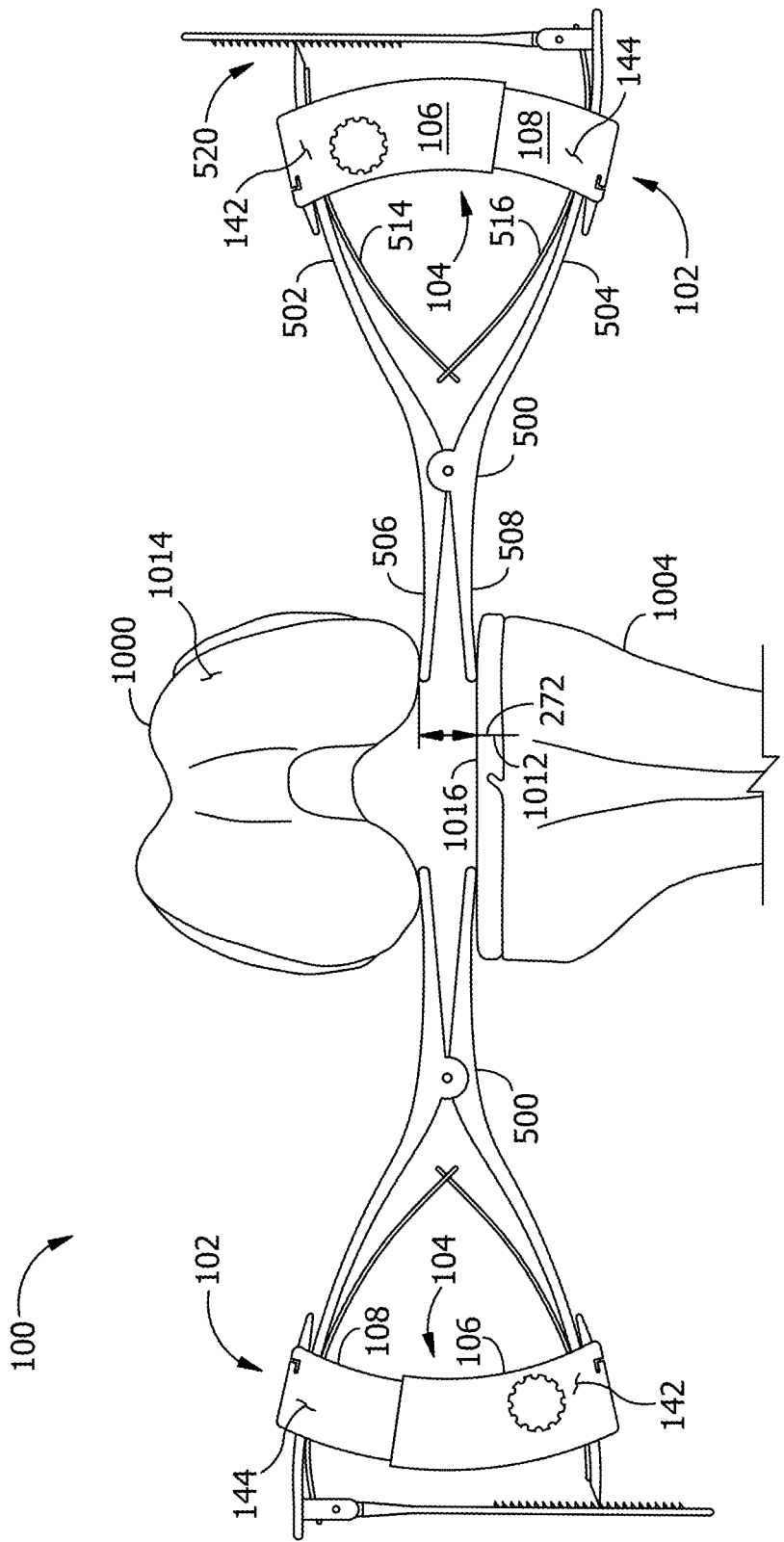
FIG. 1 is a schematic view of parts of a flexed knee joint prior to removal of bone and cartilage for a knee arthroplasty or other surgical procedure, showing two surgical spreaders having spreader jaws inserted in a gap between the distal end of the femur and the proximal end of the tibia, a first example measurement instrument attached to the spreader handgrips of one of the surgical spreaders, and a second example measurement instrument attached to the spreader handgrips of the other surgical spreader.

The disclosed apparatus embodiments of the measurement instrument of the invention measure and communicate mechanical forces and relative spatial displacements of the jaws and/or handgrips of a manually-operated surgical spreader. The disclosed apparatus includes a measurement instrument having a telescoping housing configured for attachment to the two opposing handgrips of a surgical spreader. The telescoping housing includes a first handgrip clamp positioned at a first handgrip end of the telescoping housing, a second handgrip clamp positioned at a second handgrip end of the telescoping housing, a displacement transducer, a force transducer, and a circuit board assembly electrically connected to the force transducer and the displacement transducer. The displacement transducer is configured to measure a spatial displacement of the first handgrip end relative to the second handgrip end. The force transducer is configured to measure magnitude and a direction of a mechanical force causing the spatial displacement of the first handgrip end relative to the second handgrip end. The circuit board assembly is configured to receive a first electrical signal from the displacement transducer and a second electrical signal from the force transducer, convert the first electrical signal to a measured value of spatial displacement, convert the second electrical signal to a measured value of mechanical force, and transmit the measured value of displacement and the measured value of mechanical force to another device.

The telescoping housing includes an outer housing and an inner housing slidably engaged with the outer housing. The outer housing includes the first handgrip end; an outer housing sliding end opposite the first handgrip end; an outer housing proximal side wall; an outer housing distal side wall; and an outer housing end wall extending from the outer housing proximal side wall to the outer housing distal side wall. The outer housing is formed with an outer housing handgrip channel extending through the first handgrip end to the outer housing end wall, through the outer housing proximal side wall, and through the outer housing distal side wall. The inner housing includes the second handgrip end; an inner housing sliding end opposite the second handgrip end; an inner housing proximal side wall; an inner housing distal side wall; and an inner housing end wall extending from the inner housing proximal side wall to the inner housing distal side wall. The inner housing is formed with an inner housing handgrip channel extending through the second handgrip end to the inner housing end wall, through the inner housing proximal side wall, and through the inner housing distal side wall. The inner housing slidably engages with the outer housing with the inner housing sliding end passing through an aperture formed through the outer housing sliding end.

The force transducer includes a clamp block slidably engaged with the outer housing; a cantilever beam having a first end affixed to the clamp block and a second end affixed to the inner housing; and a strain gauge affixed to the cantilever beam. The strain gauge is configured to measure a mechanical force causing a deflection of the first end of said cantilever beam relative to said second end of said cantilever beam and output the second electrical signal. A force measurement actuator enables measurement of mechanical forces causing displacement of the inner housing relative to the outer housing. The force measurement actuator optionally includes a force transducer clamp knob having a threaded shaft engaged with a threaded aperture formed in the outer housing; and a force transducer clamp plate positioned for contact with the threaded shaft and for sliding contact with the clamp block. The clamp block may be immobilized against the outer enclosure by sufficient advancement of the threaded shaft against the force transducer clamp plate, thereby enabling a measurement of mechanical force causing a displacement of the outer housing relative to the inner housing.

When mechanically activated, the force transducer provides accurate measurements over a displacement range sufficient for adjustment of components of a joint prosthesis such as an artificial knee joint. When mechanically deactivated, the telescoping housing is free to move over the entire range of movement of the spreader handgrips without applying mechanical stress to the force transducer, thereby allowing the measurement instrument to made more compact and force measurements to be more accurate during measurements of joint anatomy and prosthesis placement and adjustment.

The displacement transducer optionally includes a stationary portion fixed to the inner housing; and a sliding armature slidably engaged with the stationary portion and rotatably coupled to the outer housing. The measurement instrument optionally further includes a first rotatable coupling attached to the outer housing; a link bar rotatably coupled to the outer housing by said first rotatable coupling; and a second rotatable coupling attached to the sliding armature. The link bar is rotatably coupled to the sliding armature by the second rotatable coupling.

The circuit board assembly optionally includes a transducer excitation circuit connected for signal communication with the force transducer and the displacement transducer; a signal conditioning circuit connected for signal communication with the force transducer and the displacement transducer; an analog to digital converter connected for signal communication with the signal conditioning circuit; and an acquisition controller connected for signal communication with said analog to digital converter and a memory. A multiplexer is optionally interposed in electrical connections between the force transducer, the displacement transducer, and the signal conditioning circuit, and may optionally be interposed in electrical connections between the force transducer, the displacement transducer, and the transducer excitation circuit.

The circuit board assembly optionally includes a wireless communications device connected for signal communication with the acquisition controller with the wireless communications device configured for wireless signal communication with another measurement instrument. The acquisition controller is configured to transmit the measured value of displacement and the measured value of force to another measurement instrument. The acquisition controller is optionally configured to store the measured value of force in a memory; store in the memory a second measured value of force received from another measurement instrument; determine a magnitude of difference between the measured value of force and the second measured value of force; activate a first status indicator when the magnitude of difference is greater than a stored threshold value; and activate a second status indicator when the magnitude of difference is less than or equal to the stored threshold value. Two or more measurement instruments may exchange measured data values to facilitate soft tissue balancing and prosthetic joint adjustment during surgical procedures.

DETAILED DESCRIPTION OF THE INVENTION

Example apparatus embodiments referred to as a measurement instrument are configured to measure forces and displacements associated with surgical spreaders commonly used in orthopedic surgery, for example knee surgery. The measurement instrument includes a telescoping enclosure having two handgrip clamps configured to attach securely to the two opposing rotatably-coupled spreader handgrips of many different types of commercially-available manually-operated surgical spreaders. Embodiments of the measurement instrument may be used with surgical spreaders having indexed locking mechanisms, surgical spreaders having continuously variable locking mechanisms, and surgical spreaders having many different types and sizes of spreader jaws, without requiring structural modification of the surgical spreaders.

When the handgrip clamps are engaged to securely attach the measurement instrument to the two opposing rotatably-coupled handgrips of a surgical spreader, the telescoping enclosure spans the distance between the opposing handgrips. Movements of the spreader handgrips relative to one another cause a corresponding displacement of the first end of the telescoping enclosure relative to the second end of the telescoping enclosure. A displacement transducer positioned inside the telescoping enclosure is configured to output an electrical signal related to spatial displacement of a first end of the telescoping enclosure relative to a second end of the telescoping enclosure. Signal conditioning circuits, an analog to digital converter, and an acquisition controller in the measurement instrument convert the electrical signal from the displacement transducer to numerical values of linear displacement which may optionally be expressed in selected engineering units such as millimeters or inches. An angular separation of the spreader jaws may optionally be determined from data measured by the linear transducer, for example an angle between opposing jaw faces with the vertex of the measured angle at the fulcrum of the surgical spreader. The displacement transducer in some embodiments provides a measurement resolution of 0.2 millimeters (0.007 inch) or better, and transducers with smaller resolution are readily available and compatible with the disclosed measurement instrument embodiments. Spatial displacements measured and reported by the displacement transducer in the measurement instrument can be presented as values corresponding to linear and/or angular displacements of the spreader jaws and spreader handgrips.

A mechanical force is needed to displace the first end of the telescoping enclosure relative to, i.e. toward or away from, the second end of the telescoping enclosure. The mechanical force may result from, for example, a force exerted by a person's hand against the spreader handgrips, a force exerted by the tissues and bones of a skeletal joint against the jaws of the surgical spreader, a force exerted by the spreader jaws against the tissues and bones of the skeletal joint, a force exerted by the spreader jaws against components of a joint prosthesis, calibration fixture or other surgical device, or a combination of some or all of these forces. Embodiments of a measurement instrument measure mechanical forces acting on or imposed by a surgical spreader by measuring a magnitude of mechanical force causing a displacement of the first end of the telescoping enclosure relative to the second end of the telescoping enclosure. A force transducer in the telescoping housing is configured to output an electrical signal related to a magnitude and direction of mechanical force applied to the first end of the telescoping housing relative to the second end of the telescoping housing. Force data may optionally be presented as a magnitude and direction of force acting on spreader jaws and/or spreader handgrips. Force data may further be presented as a difference in mechanical forces measured by two measurement instruments coupled to two surgical spreaders being used for balancing ligaments and other aspects of a natural or prosthetic joint.

Force and displacement data acquired by a measurement instrument can be transmitted wirelessly to a remoted monitoring system and/or another measurement instrument. Force and measurement data is acquired and transmitted to a display device for viewing in human-readable form sufficiently quickly that a surgeon can see data values change in near real-time, i.e., without time delays that could slow surgical procedures. For example, the disclosed embodiments are capable of measuring and reporting force and displacement data in less than 0.2 second, faster than average human response time. Because of the fast measurement response and data accuracy, the disclosed example measurement instrument embodiments are effective for measuring and establishing preferred separation distances between the surfaces of bones in a knee joint and between components of a prosthetic knee joint. The disclosed example measurement instrument embodiments are further effective for soft tissue balancing by accurately measuring forces acting on surgical spreaders positioned on opposite sides of a natural or prosthetic knee joint, and for measuring forces acting on or imposed by other anatomical features or prosthesis components.

Figure 2:
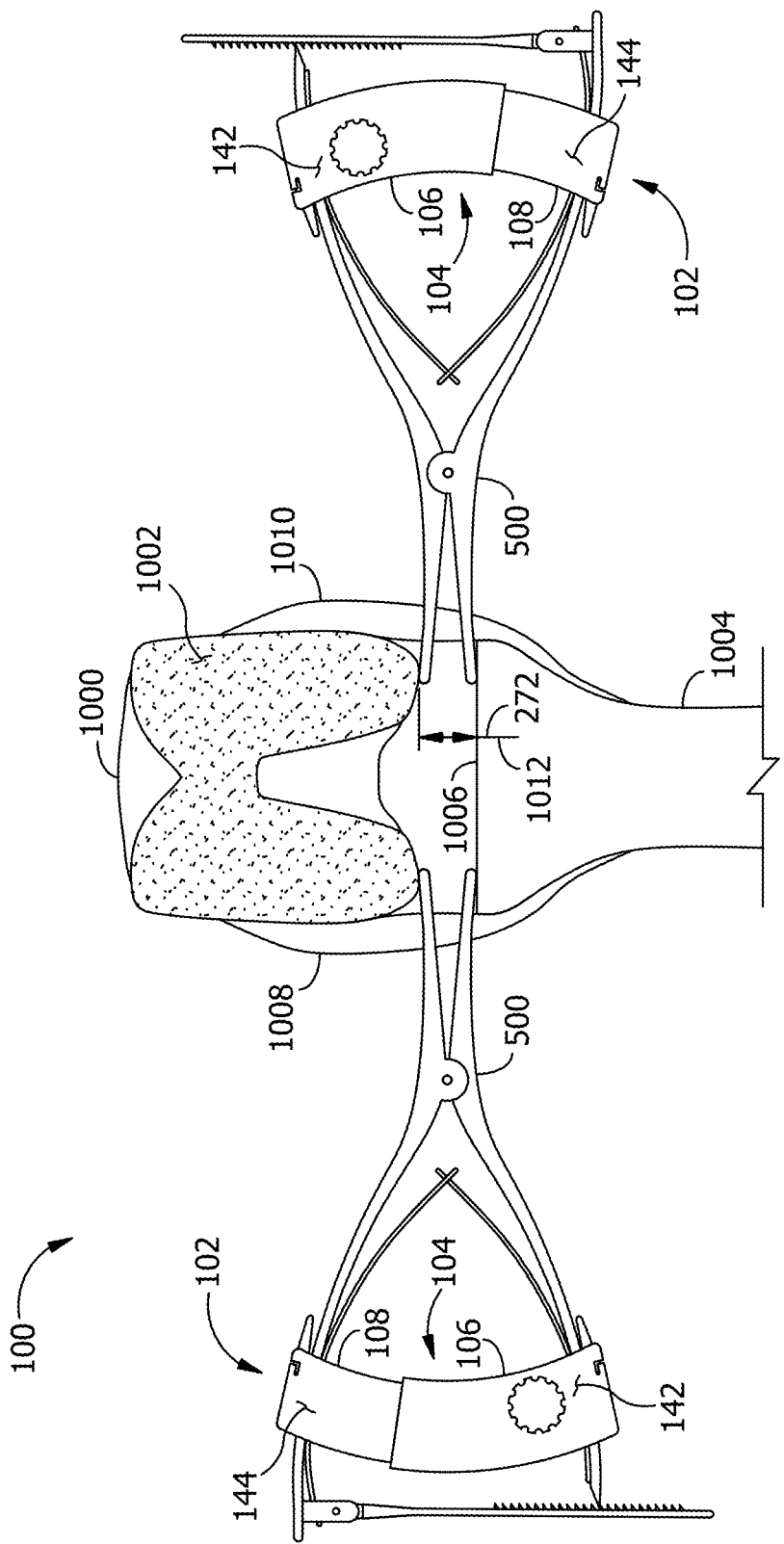
FIG. 2 is a schematic view toward examples of a surgically modified distal end of a femur, a surgically modified proximal end of a tibia, and two surgical spreaders inserted in a gap between the ends of the femur and tibia, with each of the surgical spreaders having attached to both spreader handgrips an example measurement instrument.

Example applications of an embodiment 100 are shown in FIG. 1 and FIG. 2. A simplified representation of a human knee joint prior to surgical removal of bone and cartilage from the femur 1000 and tibia 1004 is shown in FIG. 1 with the distal end 1014 of the femur facing the viewer and the tibia extending downward at a substantial angle to the femur. For discussion purposes herein, the examples of FIG. 1 and FIG. 2 apply to use of an embodiment 100 for procedures on a left knee or a right knee. The patella, ligaments, muscles, and other tissues near the knee joint have been omitted from FIG. 1 and FIG. 2. A first surgical spreader 500 is shown with its spreader jaws (506, 508) inserted into a gap 1012 between the femur and cartilage 1016 on the proximal end of the tibia. A second surgical spreader 500 is shown with its spreader jaws inserted into the gap 1012 on a side of the knee joint laterally opposite the first surgical spreader. Both example surgical spreaders are of the type with spreader jaws that move apart from one another as the spreader handgrips (502, 504) are manually moved toward one another by a surgeon's hand. The spreader handgrips on both surgical spreaders have been adjusted to place the outer surfaces of the spreader jaws in contact with the femur and tibia. A separation distance 272 between external surfaces of the spreader jaws may represent a dimension of the gap 1012 to be measured and/or modified by a surgical procedure.

FIG. 1 shows two units of an example apparatus embodiment referred to as a measurement instrument 102. A first measurement instrument 102 is shown securely attached to both handgrips of a first surgical spreader 500 with the measurement instrument spanning a separation distance corresponding to the size of a gap between the spreader handgrips. The separation distance between the spreader handgrips varies in response to manual operation of the surgical spreader by a person holding the surgical spreader. A second measurement instrument 102 is similarly attached to the handgrips of a second surgical spreader 500. The example measurement instrument 102 includes a telescoping enclosure 104 having an outer housing 106 and an inner housing 108 slidably engaged with the outer housing. The measurement instruments 102 in the example of FIG. 1 are both shown in a view toward an exterior surface of the outer housing front wall 142 and the exterior surface of the inner housing front wall 144 of the telescoping enclosure 104. An apparatus embodiment 100 includes the measurement instrument 102 and optionally includes a surgical spreader 500.

FIG. 2 shows an example of two surgical spreaders 500 and two measurement instruments 102 positioned to perform measurements and movements of a knee joint as in FIG. 1, but with a surgically modified distal end 1002 of the femur 1000 and a surgically modified proximal end 1006 of the tibia 1004. In the example of FIG. 2, bone, cartilage, and other tissue have been removed from the ends of the femur and tibia to form surfaces for placement of components for a prosthetic knee joint. A first collateral ligament 1008 and a second collateral ligament 1010 are shown at the surgically modified knee joint to illustrate that two embodiments 100 may be used for ligament balancing by simultaneous, precise, and accurate measurement of spreader jaw separation distances 272, the corresponding gap distance 1012 between the femur and tibia, forces exerted by the surgical spreaders against the knee joint, and forces exerted by the knee joint against the surgical spreaders. Although the measurement instruments 102 and surgical spreaders 500 in FIGS. 1 and 2 have been positioned with the outer housing front walls 142 facing toward the viewer for both measurement instruments, one or both of the surgical spreaders could alternately be positioned with the outer housing front walls 142 facing away from the viewer, at the discretion of the surgeon performing the procedure.

Figure 3:
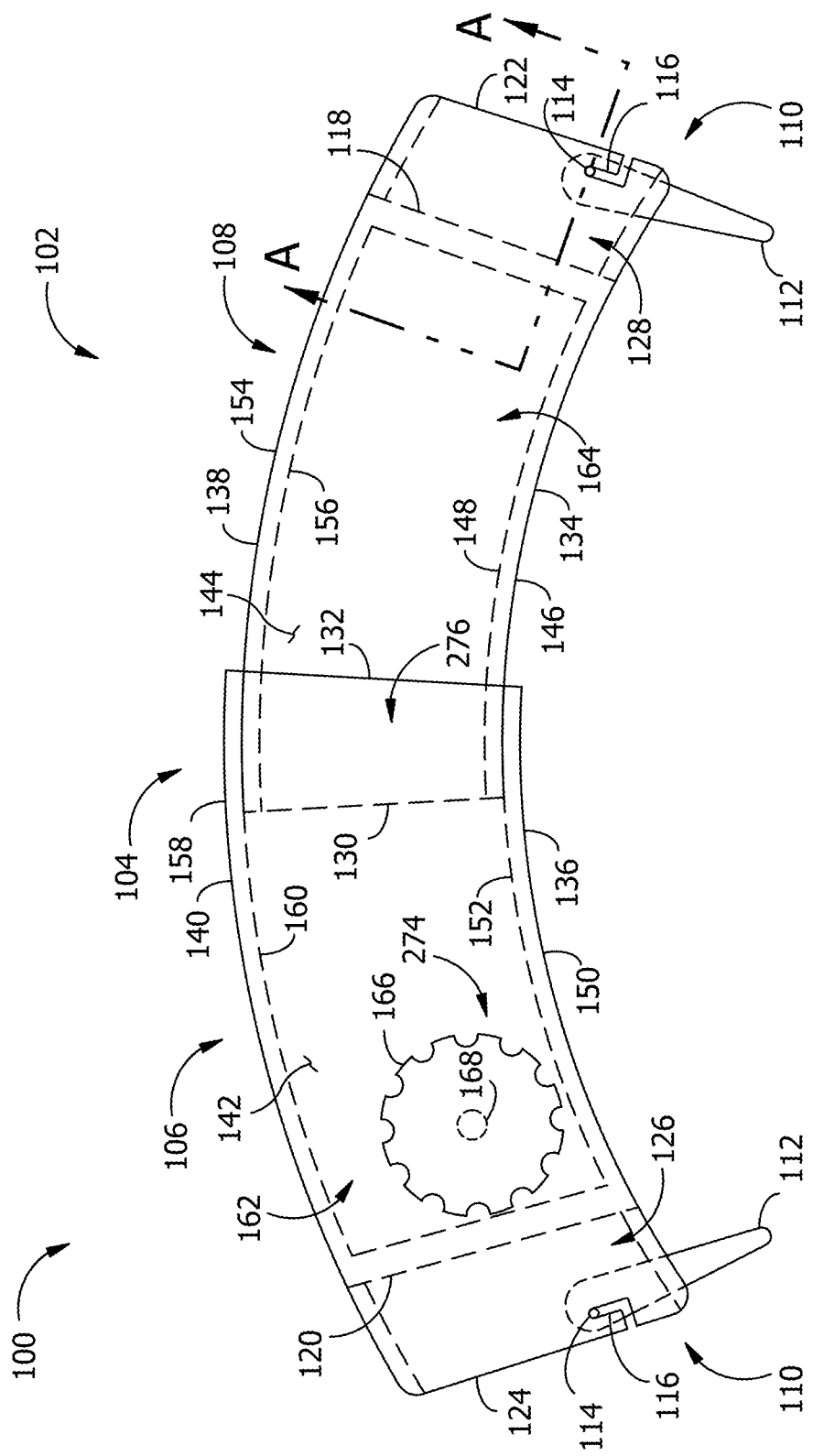
FIG. 3 is a view toward the exterior front surfaces of a telescoping enclosure for a measurement instrument embodiment having handgrip clamps positioned to secure the measurement instrument to both spreader handgrips of a surgical spreader.

Some additional features of the example measurement instrument 102 are shown in FIG. 3. The telescoping enclosure 104 has an inner housing handgrip channel 128 formed at a handgrip end 122 of the inner housing 108. The inner housing handgrip channel extends from the inner housing handgrip end 122 to an inner housing end wall 118 inside the inner housing 108. The inner housing handgrip channel 128 also extends to and through the exterior surface 146 of the inner housing proximal side wall 134 and the exterior surface 154 of the inner housing distal side wall 138. The inner housing end wall 118 is joined at one end to the inner housing distal side wall 138 and at a transversely opposite end to the inner housing proximal side wall 134. The inner housing proximal side wall 134 will be the side of the inner housing 108 nearest the spreader jaws when the measurement instrument 102 is attached to a surgical spreader. A handgrip clamp lever 112 having a clamp lever fulcrum 114 slidably engaged with an "L"-shaped clamp lever slot 116 passing through edges of the inner housing handgrip end 122 forms one of two handgrip clamps 110 on the telescoping enclosure 102.

As shown in FIG. 3, the example telescoping enclosure further includes an outer housing handgrip channel 126 formed at a handgrip end 124 of the outer housing 106. The outer housing handgrip end 124 may also be referred to as the first handgrip end of the telescoping enclosure 104 and the inner housing handgrip end 122 may be referred to as the second handgrip end of the telescoping enclosure. The outer housing handgrip channel 126 extends from the outer housing handgrip end 124 to an outer housing end wall 120 inside the outer housing 106. The outer housing handgrip channel 126 also extends to and through the proximal side wall exterior surface 150 and the distal side wall exterior surface 158 of the outer housing 106. The outer housing end wall 120 is joined at one end to an outer housing distal side wall 140 and at a transversely opposite end to an outer housing proximal side wall 136. Another handgrip clamp lever 112 having its clamp lever fulcrum 114 slidably engaged with an "L"-shaped clamp lever slot 116 passing through an edge of the outer housing handgrip end 124 forms a second of two handgrip clamps 110 on the telescoping enclosure 102.

An aperture 276 formed at the outer housing sliding end 132 is sized to admit the inner housing 108, placing an interior void space 164 of the inner housing in fluid communication with an interior void space 162 of the outer housing and positioning an inner housing sliding end 130 inside the interior void space 162 of the outer housing 106. The outer housing sliding end 132 is positioned against exterior surfaces of the inner housing. An exterior surface 154 of the inner housing distal side wall 138 is in sliding contact with an interior surface 160 of the outer housing distal side wall 140. An exterior surface 146 of the inner housing proximal side wall 134 is in sliding contact with an interior surface 152 of the outer housing proximal side wall 136. The inner housing 108 preferably engages the outer housing 106 with a sliding fit.

An interior surface 156 of the inner housing distal side wall 138, an interior surface 148 of the inner housing proximal side wall 134, the inner housing end wall 118, the front wall 144 of the inner housing front cover, a back wall of the inner housing back cover 194, and the sliding end 130 of the inner housing form the boundaries of the interior void space 164 of the inner housing. The interior surface 160 of the outer housing distal side wall 140, the interior surface 152 of the outer housing proximal side wall 136, the outer housing sliding end 132, a front wall of the outer housing front cover 188, a back wall of the outer housing back cover 190, and the outer housing end wall 120 form the boundaries of the interior void space 162 of the outer housing.

FIG. 4 and FIG. 5 illustrate an example of one of many types of commercially available surgical spreaders suitable for use with the disclosed embodiments 100. The example surgical spreader 500 includes a first spreader handgrip 502 rotatably joined to a second spreader handgrip 504 at a handgrip rotational joint 510. The handgrip rotational joint 510 may include a fulcrum 512 coupling the two spreader handgrips to one another. The first spreader handgrip 502 is joined to or integrally formed with a first spreader jaw 506. The second spreader handgrip 504 is joined to or integrally formed with a second spreader jaw 508. Each of the first and second spreader jaws is formed with an exterior jaw surface 534. Some surgical spreaders include a first handgrip spring 514 and a second handgrip spring 516 arranged to urge the first and second spreader jaws toward one another. Some surgical spreaders omit one or both of the handgrip springs. The handgrip springs may be attached to the spreader handgrips by spring fasteners 518 holding each handgrip spring securely to each spreader handgrip.

A surgical spreader 500 may include a spreader handgrip locking mechanism 520 for holding the spreader handgrips and spreader jaws stationary relative to one another. The spreader handgrip locking mechanism 520 may include a tapered end 528 formed at an end of the first spreader handgrip 502 and a clamp bar 530 rotatably coupled to the second spreader handgrip 504. The tapered end 528 may be shaped to engage with one of many ratchet teeth 526 formed on the clamp bar 530. The ratchet teeth 526 may be formed as ridges projecting outward from the clamp bar 530 or as grooves or channels formed in the clamp bar. A handgrip post 524 extending from the second spreader handgrip includes a rotatable joint 522 coupling the clamp bar to the handgrip post. The tapered end 528 of the first handgrip may be engaged with a selected ratchet tooth 526 to hold the first and second spreader jaws (506, 508) at a preferred separation distance from one another. The clamp bar 530 may be rotated away from contact with the first spreader handgrip 502 when the clamping feature is not being used to hold the spreader handgrips and spreader jaws stationary relative to one another.

Figure 6:
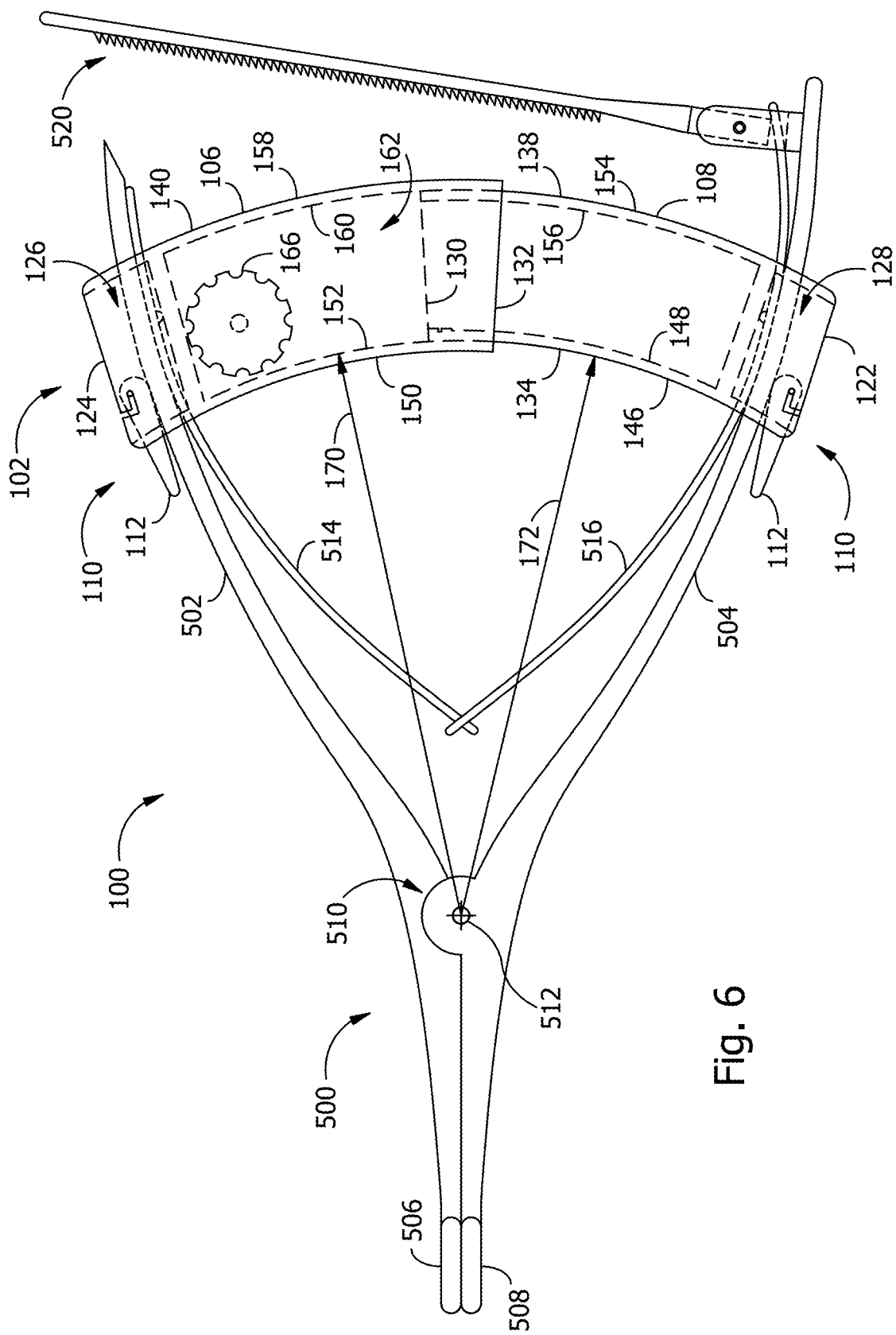
FIG. 6 illustrates an example of the measurement instrument of FIGS. 1, 2, and 3 strongly attached to the two spreader handgrips of the example surgical spreader of FIG. 4 with the two spreader jaws closed against one another, the spreader handgrips at their maximum separation distance from one another, and the telescoping enclosure of the measurement instrument extended to span the separation distance of the spreader handgrips.

For surgical spreaders having springs (514, 516) disposed in the space between the opposing spreader handgrips as suggested in the figures, the example embodiments of the measurement instrument 102 are preferably coupled to the spreader handgrips in close proximity to the spring fasteners 518 (ref. FIG. 4) to avoid interfering with the action of the handgrip springs (514, 516) and with operation of the spreader handgrip locking mechanism 520. An example of preferred attachment of the measurement instrument to a surgical spreader with handgrip springs is shown in FIG. 6, where the portion of a handgrip spring held in close contact with a spreader handgrip by a spring fastener 518 is positioned about midway along the longest dimension of the outer housing handgrip channel 126. As suggested in the example of FIG. 6, the measurement instrument 102 is securely clamped to the first spreader handgrip 502 and the second spreader handgrip 504 by the two handgrip clamps 110. In the preferred attachment position, the radius of curvature 172 of the exterior surface 146 of the inner housing proximal side wall 134 will be centered close to the rotational center of the handgrip rotational joint 510 and the radius of curvature 170 of the interior surface 152 of the outer housing proximal side wall 136 will also be centered close to the rotational center of the handgrip rotational joint, thereby facilitating smooth sliding movement between the outer housing and inner housing as the spreader handgrips are moved relative to one another.

Some alternative surgical spreaders position the handgrip springs and a spreader handgrip locking mechanism in close proximity to the fulcrum rather than at the ends of the handgrips as shown in the example figures. For such alternative medical spreaders, a measurement instrument 102 will preferably be attached by the handgrip clamps 110 near the ends of the spreader handgrips approximately as shown in the figures, with the handgrip springs and handgrip clamp mechanism interposed between the measurement instrument and the fulcrum for the alternative surgical spreader.

Figure 7:
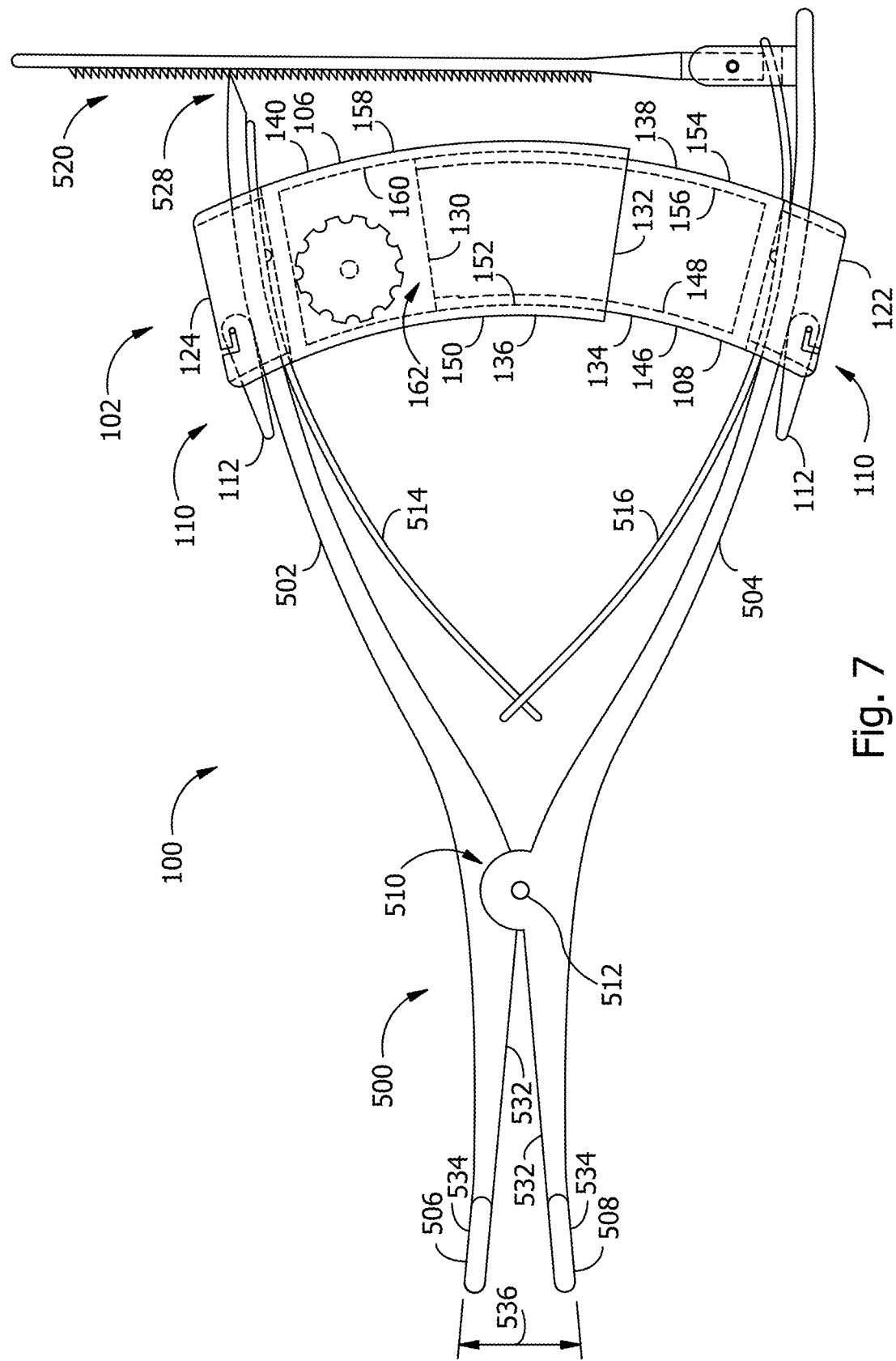
FIG. 7 continues the example of FIG. 6, showing an example of the spreader handgrips displaced toward one another, the spreader jaws displaced apart from one another, and an outer housing and an inner housing forming parts of the telescoping enclosure displaced toward one another by movement of the spreader handgrips.

FIG. 7 continues the example of FIG. 6, showing an example of the first spreader handgrip 502 displaced toward the opposing second spreader handgrip 504, causing the first spreader jaw 506 to be displaced away from the opposing second spreader jaw 508 by a jaw separation distance 536 measured at selected reference points on the exterior surfaces 534 of the jaws. Displacing the first spreader jaw away from the second spreader jaw introduces a gap between the interior jaw surfaces 532 of the opposing spreader jaws. A comparison of FIG. 7 to FIG. 6 shows that the tapered end 528 of the first handgrip 502 is closer to the second handgrip 504 in FIG. 7 than in FIG. 6, and the sliding end 130 of the inner housing 108 is farther from the sliding end 132 of the outer housing 106, consistent with repositioning of the inner housing farther into the interior of the outer housing as the separation distance between the spreader handgrips is reduced. FIG. 7 further illustrates an example of the spreader handgrip locking mechanism 520 engaged to hold the spreader jaws (506, 508) stationary relative to one another at a separation distance 536 selected by a person using the apparatus 100.

Figure 8:
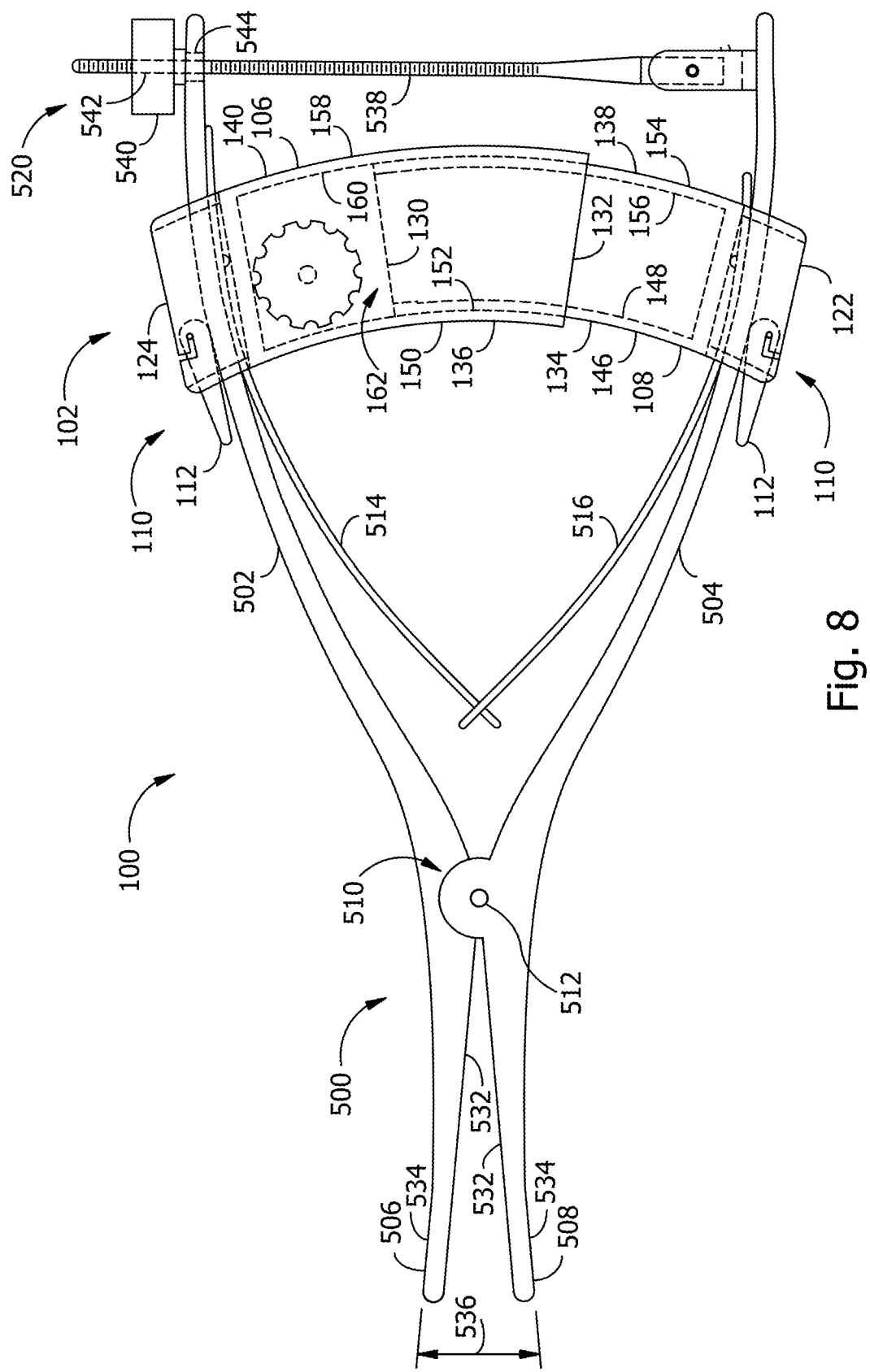
FIG. 8 shows the example measurement instrument of the previous figures attached to another example of a surgical spreader having a continuously variable indexing mechanism with a handgrip clamp fitted with a threaded clamp rod and a handgrip locking knob for holding the spreader handgrips at a selected separation distance from one another.

FIG. 8 shows the example measurement instrument 102 of the previous figures attached by two handgrip clamps 110 to the spreader handgrips (502, 504) of another form of a surgical spreader 500. The example surgical spreader 500 of FIG. 8 includes an alternative form of a spreader handgrip locking mechanism 520 having a threaded clamp rod 538 rotatably coupled to the second spreader handgrip 504. An end of the threaded clamp rod 538 passes through an aperture 544 formed in the first spreader handgrip 502. A handgrip locking knob 540 formed with a threaded aperture 542 engages with the threaded clamp rod 538. The handgrip locking knob 540 may be positioned on the threaded clamp rod to adjust the spreader jaws (506, 508) to a continuously adjustable separation distance 536. The handgrip springs (514, 516) act in opposition to the compression force exerted by the handgrip locking knob 540, cooperating with the handgrip locking knob to hold the spreader jaws at a selected separation distance. As for other surgical spreaders compatible with the disclosed embodiments 100, the measurement instrument measures and reports the separation distance 536 of the spreader jaws and forces acting on and/or exerted by the spreader jaws. FIG. 8 further represents an example of a surgical spreader with straight spreader jaws instead of the curved spreader jaws shown in other figures. The disclosed apparatus embodiments 100 are effective for measuring force and displacement values for surgical spreaders of many different handgrip and/or blade shapes, curvatures, and lengths.

Figure 10:
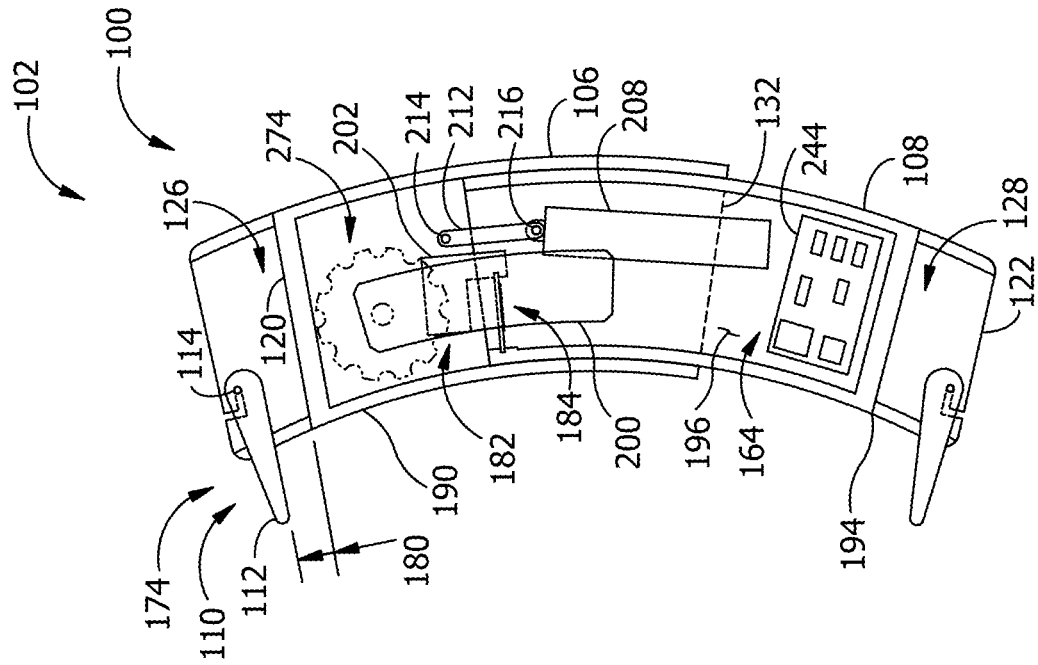
FIG. 10 continues the example of FIG. 9, showing examples of the inner housing slidably displaced further into the outer housing with related position changes of parts of the displacement transducer and force transducer.
Figure 9:
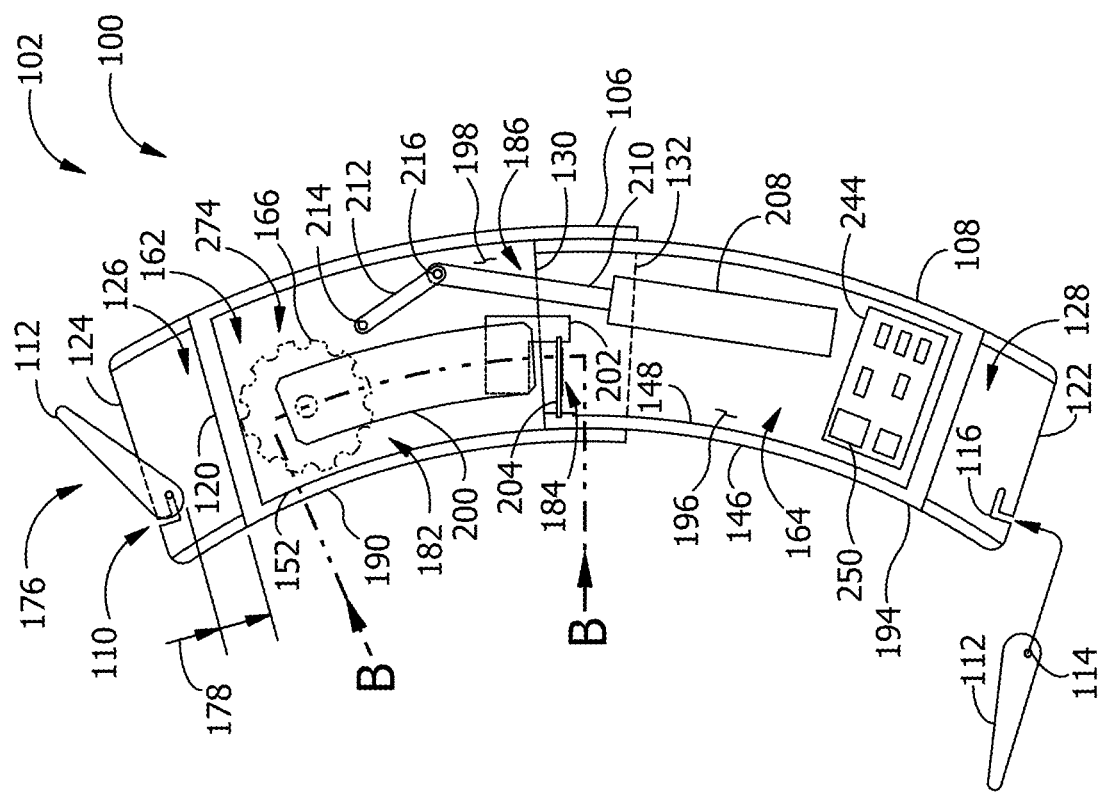
FIG. 9 is a schematic view of the example measurement instrument showing examples of a force transducer, a displacement transducer, two handgrip clamps, and a force measurement actuator coupled to the inner housing and outer housing of the telescoping enclosure.

FIG. 9 and FIG. 10 show examples of some internal details of the measurement instrument 102. In the examples of FIGS. 9-10, the view is toward an interior surface 198 of the outer housing back cover 190 and an interior surface 196 of the inner housing back cover 194. The outer housing front cover 188 and inner housing front cover 192 (ref. FIG. 14) have been omitted from FIGS. 9-10 to expose components positioned in the interior void space 164 of the inner housing 108 and in the interior void space 162 of the outer housing 106.

FIGS. 9-13 show examples of handgrip clamps 110 for securing the measurement instrument 102 to both handgrips of a surgical spreader. A first handgrip clamp lever 112 is shown at the handgrip end 124 of the outer housing 106 in an example unlocked position 176 in FIG. 9 and an example locked position 174 in FIG. 10. A gap 178 between the handgrip clamp lever and the outer housing end wall 120 is larger in the example unlocked position 176 than the corresponding gap 180 in the locked position 174. In the unlocked position, the handgrip clamp lever does not press firmly against a spreader handgrip placed in the handgrip channel 126 and the spreader handgrip and measurement instrument may move relative to one another. In the locked position, the eccentric rotation of the clamp lever fulcrum 114 forces the handgrip clamp lever 112 into very firm contact with a spreader handgrip positioned in the handgrip channel, immobilizing the spreader handgrip between the handgrip clamp lever and the outer housing end wall 120. The handgrip clamp lever 112 at the handgrip end 122 of the inner housing 108 functions in a similar manner. As shown in FIG. 9, the handgrip clamp lever 112 may be removed from the clamp lever slot 116. Removing the handgrip clamp levers enables easy placement of the spreader handgrips into the handgrip channels. After a spreader handgrip is placed in a handgrip channel, the handgrip clamp lever may be re-engaged in the clamp lever slot and the handgrip clamp lever rotated to its locked position 174 to immobilize the spreader handgrip in the handgrip channel.

FIGS. 11-12 show an example of the handgrip clamp lever 112. The handgrip clamp lever 112 is formed at one end with a handgrip contact face having a selected radius of curvature 222 and a clamp lever fulcrum 114 joined to, or alternately formed as an integral part of, the handgrip clamp lever. The clamp lever fulcrum 114 extends outward from a top side and from a bottom side of the handgrip clamp lever 112. A rotational axis 224 of the clamp lever fulcrum is positioned an offset separation distance 226 from the center of curvature 220 of the cylindrical surface 218. A handgrip clamp lever 112 may alternatively be made with a different surface curvature than the cylindrical surface 218, for example a surface shaped to control an increase or decrease in a mechanical force exerted by the clamp lever against the handgrip of a surgical spreader as the handgrip clamp is operated. The offset distance 226 and radius of curvature 222 are preferably selected to provide a magnitude of contact force sufficient to immobilize a surgical spreader handgrip relative to the measurement instrument when the measurement instrument is attached to a surgical spreader for making force and displacement measurements with an embodiment 100.

An example of engagement of the handgrip clamp lever 112 to the inner housing 108 of the measurement instrument 102 is shown in FIG. 13. FIG. 13 shows a partial cross-sectional view A-A through the inner housing back cover 194 and the inner housing front cover 192. When attached to one another, the inner housing back cover 194 and inner housing front cover 192 form the inner housing 108. The handgrip clamp lever fits into the inner housing handgrip channel 128 with the handgrip clamp fulcrum 114 engaged in the clamp lever slot 116, forming a space 180 in the handgrip channel into which a spreader handgrip may be positioned and secured by the handgrip clamp lever 112. The removable engagement between a second handgrip clamp lever 112 and the clamp lever slot 116 formed in the outer housing 106 is similar to the example shown in FIG. 13 for the inner housing 108.

After being connected to the handgrips of a surgical spreader by the handgrip clamp levers, the inner housing 108 slides in and out of the outer housing 106 in response to movements of the spreader handgrips. Displacements of the inner housing relative to the outer housing, corresponding to displacements of the spreader handgrips and spreader jaws, are measured by a displacement transducer in the measurement instrument. Returning to FIG. 9 and FIG. 10, the displacement transducer 186 may include a linear variable displacement transducer (LVDT) having a stationary portion 208 attached to and stationary with respect to an interior surface of the inner housing 108, for example the interior surface 196 of the inner housing back cover 194, and a sliding armature 210 configured for sliding engagement with the stationary portion 208. In FIG. 10, the sliding armature 210 has been displaced into the interior of the stationary portion 208, with the rotatable coupling 216 of the sliding armature to a link bar 212 still visible. Movements of the sliding armature 210 relative to the stationary portion 208 cause the displacement transducer 186 to output an electrical signal representative of a linear distance by which the armature 210 has moved relative to the stationary portion. The link bar 212 rotatably connected to the outer housing 106 at a first rotatable coupling 214 and connected to the armature 210 at the second rotatable coupling 216 drives movement of the sliding armature 210 in response to displacements of the outer housing relative to the inner housing, for example when the handgrips of the surgical spreader are moved relative to one another. Electrical signals communicated between the displacement transducer 186 and an acquisition controller 250 on a circuit board assembly 244 may be used to determine and report a distance by which the first spreader handgrip has been moved relative to the second spreader handgrip, from which the distance 536 representing relative displacement of the two spreader jaws may be determined. Measured displacements of the surgical jaws may correspond to, for example, measured separation distances of the femur and tibia and/or measured separation distances between components of a prosthetic joint.

In addition to the displacement transducer 186, the measurement instrument 102 preferably includes a force transducer 184. The example force transducer 184 is configured to measure a compression force exerted against the handgrips of the surgical spreader, for example a compression force exerted by a person's hand squeezing the spreader handgrips together to cause the spreader jaws to separate. The example force transducer is further configured to measure a compression force exerted against the external surfaces 534 of the spreader jaws (506, 508), for example a force exerted against the spreader jaws by bones, ligaments, and other tissues associated with a knee joint, and a force exerted against the spreader jaws by components of a knee prosthesis. As shown in FIGS. 9-10 and FIGS. 14-16, the example force transducer 184 includes a cantilever beam 204 attached at one end 232 to an interior fixed part of the inner housing 108. The opposite end 230 of the cantilever beam 204 is attached to a clamp block 202 in contact with and slidably engaged with an interior surface of the outer housing 106. A strain gauge 206 affixed to the cantilever beam 204 outputs a signal from which forces acting to bend the cantilever beam may be determined by applying well-known engineering methods for calculating deflections of cantilever beams having known dimensions and material properties.

When the clamp block 202 is immobilized relative to the outer housing 106 by a force measurement actuator 274, the cantilever beam deflects in one direction by compression of one spreader handgrip toward the other spreader handgrip and in an opposite direction by compression of one spreader jaw toward the other spreader jaw. The ability to measure forces in both directions implies that an embodiment 100 using two surgical spreaders and two measurement instruments at the same time may be used to balance forces applied by a surgical spreader on one side of a knee joint to forces applied by another surgical spreader on a laterally opposite side of the knee joint, for natural knee joints, surgically modified knee joints, and components of knee prostheses. Examples of two surgical spreaders and two measurement instruments in simultaneous use for concurrent real-time measurements have been presented in FIGS. 1-2.

The force transducer 184 is configured to measure compression forces against the spreader handgrips and spreader jaws when the force transducer clamp block 202 is held stationary relative to the outer housing 106 by a force measurement actuator 274. When the force measurement actuator 274 is sufficiently loosened to permit the force transducer clamp block to slide freely over the interior surfaces of the telescoping enclosure 104, the separation of the spreader handgrips may be set anywhere within their range of movement without requiring the force transducer 184 to be configured for high precision measurements over the full range of spreader handgrip movement. This feature of the force transducer clamp assembly 182 and the force transducer 184 allows high precision force measurements over a selected portion of the full range of handgrip movement while providing the functionality of the measurement instrument in a compact telescoping enclosure.

An example of a force measurement actuator 274 is shown in schematic form in FIGS. 9, 10, and 14-16. An example embodiment of the force actuator 274 includes a force transducer clamp knob 166, a clamp knob threaded shaft 168 strongly affixed to the force transducer clamp knob, a threaded aperture 228 formed in the outer housing front cover through which the clamp knob threaded shaft passes, and a force transducer clamp plate 200 positioned for contact with the force transducer clamp knob 168 and a force transducer clamp block 202. FIG. 14 shows the force transducer clamp block 202 held immobile against the interior surface 198 of the outer housing back cover 190 by operation of the force measurement actuator 274 to immobilize the force transducer clamp block 202 to the interior surface 198 of the outer housing back cover. The force transducer clamp block may optionally be in sliding contact with the interior surface 196 of the inner housing back cover 194 along a portion of the interior surface 196. An end of the cantilever beam 204 is affixed to the clamp block 202. An opposite end 232 of the force transducer cantilever beam 204 attached to the inner housing 108 as shown in FIGS. 9-10 and 15-16. The strain gauge 206 is affixed to the force transducer cantilever beam 204.

Continuing with FIG. 14, the force transducer clamp knob 166 may be turned to advance the clamp knob threaded shaft 168 until the threaded shaft presses the force transducer clamp plate 200 against the force transducer clamp block 202 with sufficient force to immobilize the force transducer clamp block against the interior surface 198 of the outer housing back cover 190. After the force transducer clamp block 202 has been immobilized, further movements of the spreader handgrips and spreader jaws relative to one another cause corresponding movements of the outer housing relative to the inner housing, resulting in a mechanical force to be applied to the cantilever beam and a deflection of the cantilever beam first end 230 relative to the cantilever bend second end 232, and further causing a change in an electrical signal from the strain gauge from which a mechanical force acting on or exerted by the spreader jaws and/or spreader handgrips can be determined. Loosening the clamp knob enables the clamp block to slide with respect to the clamp plate 200 and outer housing 106, allowing the cantilever beam to return to its undeflected (i.e., straight) configuration as in FIG. 15, enabling substantial movements of the handgrips and jaws without exceeding operating limits of the force transducer 184.

Figure 15:
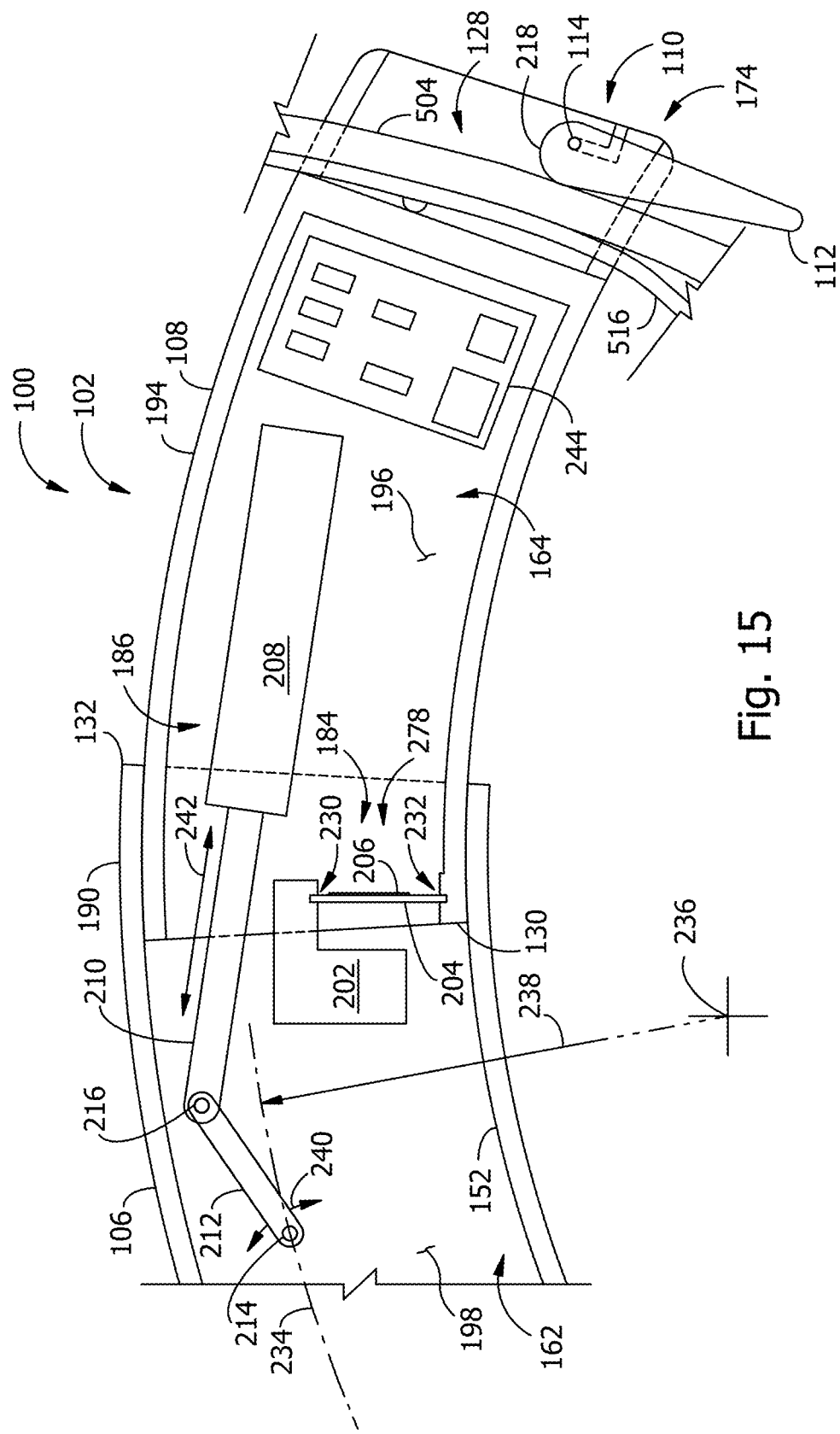
FIG. 15 is a partial schematic view toward the interior surfaces of the outer housing back cover and inner housing back cover, showing examples of the force transducer, the displacement transducer, the handgrip clamp coupled to the inner housing, a printed circuit board assembly for acquiring and communicating measurement data from the force transducer and displacement transducer, and a short segment of a spreader handgrip held stationary relative to the inner housing by the handgrip clamp.
Figure 16:
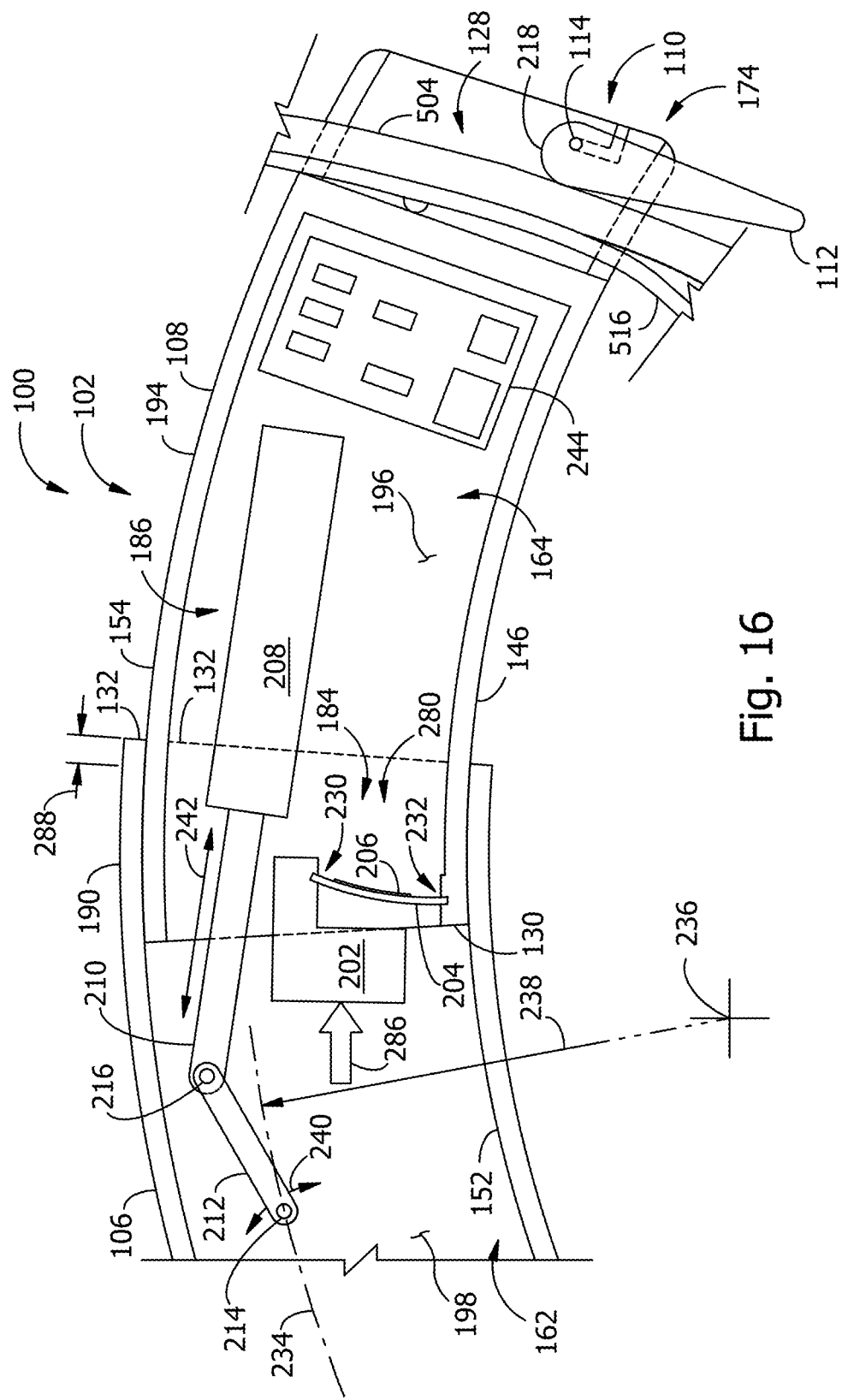
FIG. 16 continues the example of FIG. 15, showing the inner housing displaced further into the outer housing and related example displacements of parts of the force transducer and displacement transducer.

FIG. 15 and FIG. 16 show examples of some additional features of the force transducer 184 and distance transducer 186. The example force transducer 184 in FIG. 15 shows the strain gauge 206 affixed to the cantilever beam 204 with the cantilever beam first end 230 affixed to the force transducer clamp block 202 and the cantilever beam second end 232 affixed to the inner housing 108. The force transducer cantilever beam 204 is shown in an undeflected position 278 in FIG. 15, representing for example a condition in which the force measurement actuator 274 is not restricting sliding movement of the force transducer clamp block across the interior surface 198 of the outer housing and forces acting on or exerted by the surgical spreader are not being measured. The first end 230 of the force transducer cantilever beam may be deflected relative to the second end 232 of the cantilever beam when the clamp block 202 is secured to the outer housing by operation of the force measurement actuator, enabling measurements of forces acting on the measurement instrument to be made. FIG. 16 shows an example of the first end 230 of the force transducer cantilever beam in a deflected position 280 relative to the second end 232 after the force measurement actuator has been tightened sufficiently to prevent the force transducer clamp block 202 from moving relative to the outer housing and the outer housing has moved relative to the inner housing by a magnitude of relative displacement 288, as may occur in response to movements of the spreader handgrips and spreader jaws.

When the force transducer clamp assembly 182 has been adjusted to immobilize the force transducer clamp block 202 to the outer housing, further movement of the inner housing relative to the outer housing, for example by the relative displacement 288, imposes a mechanical force on the force transducer clamp block 202 that results in deflection of the force transducer cantilever beam 204 and output of an electrical signal from the strain gauge 206. In the example of FIGS. 15-16, the relative displacement of the cantilever beam first end 230 to the cantilever beam second end 232 is the same magnitude of relative displacement 288 as for the movements of the inner housing and outer housing and for the corresponding change in position of the force transducer clamp block 202. A mechanical force sufficient to cause the displacement 288, corresponding to the measurement of mechanical force to be performed by the force transducer 184 and other components in the measurement instrument 102, is represented symbolically in FIG. 16 by an outlined arrow 286.

FIG. 15 and FIG. 16 further illustrate an example of operation of the displacement transducer 186. The example displacement transducer in FIG. 15 has the stationary part 208 affixed to the inner housing and the armature 210 coupled to the outer housing by an intervening rotatable link 212. As the spreader handgrips are moved relative to one another, the rotatable coupling 214 attaching the rotatable link 212 to the outer housing follows an arcuate path 234 corresponding to a circular arc with a radius 238 from the center of rotation 236 of the handgrip rotational joint 510 of the surgical spreader 500. The rotatable link moves through an angular deflection 240 while the armature 210 moves smoothly inward and/or outward along a linear path 242. Compared to FIG. 15, the sliding armature 210 in FIG. 16 has been pushed into the stationary portion 208 in response to the inner housing 108 being pushed further into the outer housing 106 by compression of the spreader handgrips.

FIG. 16 also illustrates an example of a spreader handgrip 504 being held firmly and without slippage in the handgrip channel 128 by the handgrip clamp 110 pressing firmly against the spreader handgrip while the handgrip clamp is in its locked position 174. The measurement instrument 102 may be removed from the spreader handgrip by rotating the handgrip clamp 110 away from its locked position until the surface 218 of the handgrip clamp lever no longer presses against the spreader handgrip, sliding the clamp lever fulcrum 114 through the clamp lever slot 116 until the handgrip clamp lever can be removed from the measurement instrument, and moving the spreader handgrip out of the handgrip channel.

Figure 17:
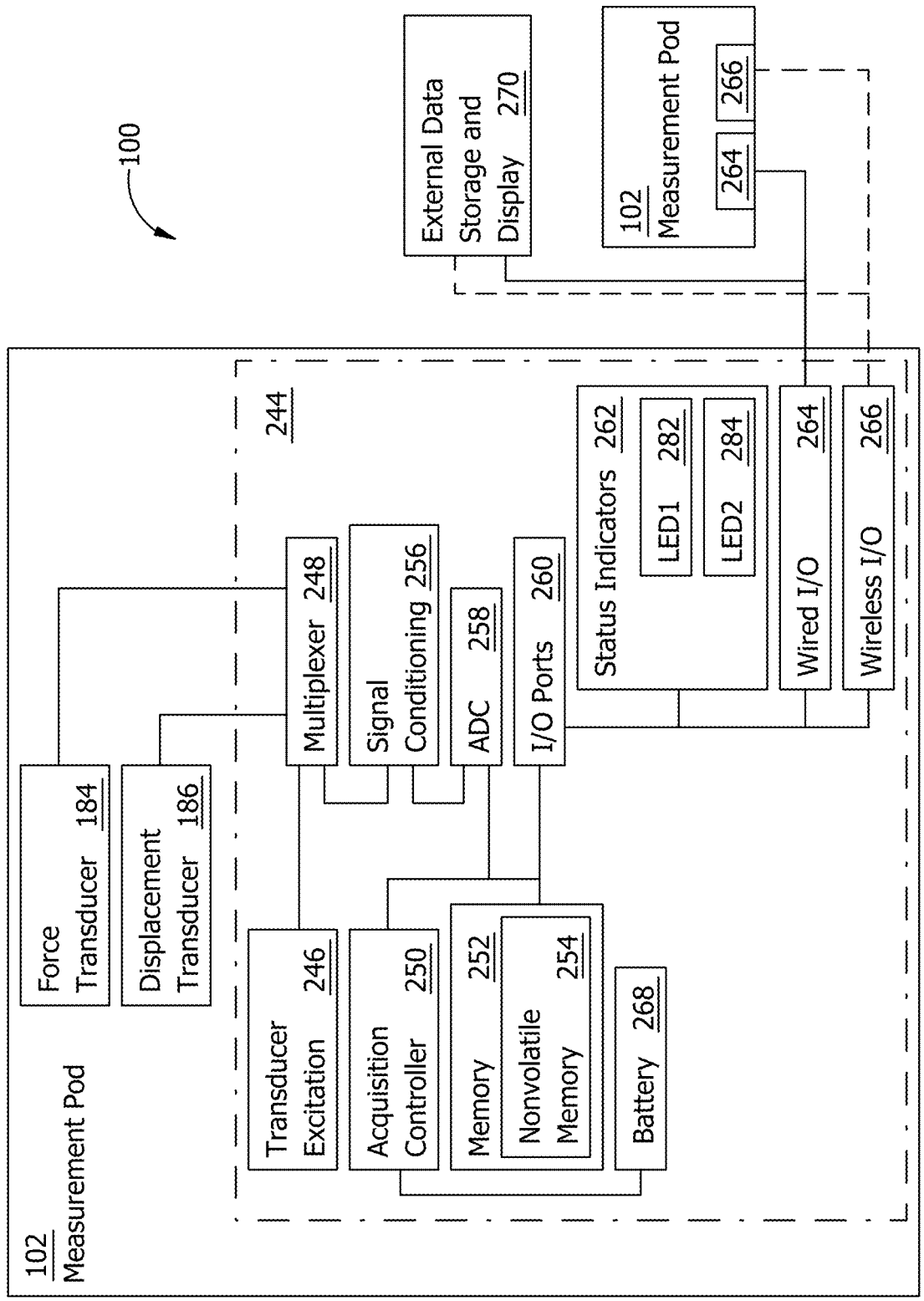
FIG. 17 is a block diagram representing electrical components and electrical connections included in an example implementation of a printed circuit board assembly positioned inside the telescoping enclosure of the measurement instrument, and further illustrating an example of two measurement instruments in electrical communication with an external data storage and display device.

FIG. 17 is a block diagram representing examples of electrical components and electrical connections included in an embodiment 100. Some of the electrical components and electrical connections may be included as part of the circuit board assembly 244. Electric power for operating the transducers and components on the circuit board assembly may be provided by an electric storage battery 268. Transducer excitation circuits 246 provide electric power connections and interface circuits needed for operation of the force transducer 184 and displacement transducer 186. Excitation circuits 246 may include, for example, a bridge circuit for the strain gauge 206 in the force transducer 184. Electrical connections to the force transducer and displacement transducer may be made directly or may optionally be made through an intervening multiplexer 248. Electrical signals representative of force data and displacement data may pass through signal conditioning circuits 256, which may include for example bandwidth-limiting analog signal filters for anti-aliasing and/or noise rejection. Analog signal output from the signal conditioning circuits 256 may be provided as input to an analog to digital converter (ADC) 258 to convert analog voltages and/or currents to digital data values.

An acquisition controller 250 stores output from the ADC 258 and retrieves operating instructions and other information from a memory 252, part of which may be configured as nonvolatile memory 254. Operations which may be performed by the acquisition controller include, for example, converting digital transducer data values received from the ADC 258 into numerical force values and numerical displacement values in preferred engineering units. The acquisition controller 250 may assert one or more status indicators 262 to provide information related to measured data. For example, the acquisition controller may assert a first light emitting diode LED1 282 when a measured parameter is within a preferred range of force values or displacement values and a second light emitting diode LED2 284 when the measured parameter is outside the preferred range. Other examples of status indicators include light emitting diodes labelled "Ready", "Sensor Limit", "Fault", and so on.

Parameter range limits, measured and/or calculated force values and displacement values, and operational status information may be transmitted from and received by the acquisition controller through a wired input and output interface (Wired I/O) 264 and/or a wireless input and output interface (Wireless I/O) 266. Examples of suitable wireless communications interfaces include, but are not limited to, Bluetooth, wifi, and IrDA.

Measured values of displacement, mechanical force and other information may optionally be exchanged between the measurement instrument 102 and another device, for example an external data storage and display device 270, one or more additional measurement instruments 102, or other communications-enabled devices. Instructions to be performed by the acquisition controller 250, measurement results, operating status, and other information may be stored in the memory 252 and optionally in the nonvolatile memory 254. Mechanical force and displacement data received by the measurement instrument 102 from another measurement instrument 102 may be stored in the memory 252. Measured values from two measurement instruments may be compared by the acquisition controller to determine a difference in measured values, from which the acquisition controller may activate a status indicator 262 when the difference is less than a stored threshold value and optionally activate another status indicator when the difference is greater than the stored threshold value. Comparison of data values from different measurement instruments, activation of indicators that are part of the measurement instrument, and display of numerical values on a remote display device are beneficial for assessing forces and displacements acting on joint anatomy or a joint prosthesis and for adjusting the joint prosthesis.

Table 1 shows examples of data obtained from operation of the disclosed embodiments 100. An external data storage and/or display device 270 may be arranged to show acquired data and calculated values for one or more measurement instruments simultaneously acquiring data and presenting measurement results during surgery. For example, the data display 270 may present parameters from a first measurement instrument 102 attached to a first surgical spreader 500 ("Instrument A" in the example figure) and a second measurement instrument attached to a second surgical spreader ("Instrument B" in the figure) in near real-time while both instrument A and instrument B are being used to set joint separation distances, measure forces applied to or acting on the surgical spreaders, and balance soft tissues during knee surgery. Displayed numerical values may be presented as measured magnitudes and/or as differences in measured magnitudes between the two instruments.

TABLE 1

Data acquirable simultaneously by two measurement instruments attached to separate surgical spreaders.

| Instrument A | | | Instrument B | | |
|---|---|---|---|---|---|
| Parameter | Value | Unit | Parameter | Value | Unit |
| Handgrip compression force | {number} | newton (N) | Handgrip compression force | {number} | N |
| Jaw Compression Force | {number} | N | Jaw Compression Force | {number} | N |
| Jaw Separation | {number} | millimeter (mm) | Jaw Separation | {number} | mm |
| Instrument B Measured Force | {number} | N | Instrument A Measured Force | {number} | N |
| Force Difference | {number} | newton (N) | {number} | | newton (N) |
| Handgrip compression pressure | {number} | pascal (Pa) | Handgrip compression pressure | {number} | Pa |
| Jaw compression pressure | {number} | Pa | Jaw compression pressure | {number} | Pa |

Unless expressly stated otherwise herein, ordinary terms have their corresponding ordinary meanings within the respective contexts of their presentations, and ordinary terms of art have their corresponding regular meanings.

GENERAL DISCLOSURES

This specification incorporates by reference all documents referred to herein and all documents filed concurrently with this specification or filed previously in connection with this application, including but not limited to such documents which are open to public inspection with this specification. All numerical quantities mentioned herein include quantities that may be plus or minus 20% of the stated amount in every case, including where percentages are mentioned. As used in this specification, the singular forms "a, an", and "the" include plural reference unless the context clearly dictates otherwise. Thus, for example, a reference to "a part" includes a plurality of such parts, and so forth. The term "comprises" and grammatical equivalents thereof are used in this specification to mean that, in addition to the features specifically identified, other features are optionally present. For example, a composition "comprising" (or "which comprises") ingredients A, B and C can contain only ingredients A, B and C, or can contain not only ingredients A, B and C but also one or more other ingredients. The term "consisting essentially of" and grammatical equivalents thereof is used herein to mean that, in addition to the features specifically identified, other features may be present which do not materially alter the claimed invention. The term "at least" followed by a number is used herein to denote the start of a range beginning with that number (which may be a range having an upper limit or no upper limit, depending on the variable being defined). For example, "at least 1" means 1 or more than 1, and "at least 80%" means 80% or more than 80%. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. Where reference is made in this specification to a method comprising two or more defined steps, the defined steps can be carried out in any order or simultaneously (except where the context excludes that possibility), and the method can optionally include one or more other steps which are carried out before any of the defined steps, between two of the defined steps, or after all the defined steps (except where the context excludes that possibility). When, in this specification, a range is given as "(a first number) to (a second number)" or "(a first number)-(a second number)", this means a range whose lower limit is the first number and whose upper limit is the second number. For example, "from 40 to 70 microns" or "40-70 microns" means a range whose lower limit is 40 microns, and whose upper limit is 70 microns.

| List of Reference Designators | |
|---|---|
| Reference Designator | Description |
| 100 | example apparatus embodiment |
| 102 | Measurement instrument |
| 104 | telescoping enclosure |
| 106 | Outer housing |
| 108 | Inner housing |
| 110 | handgrip clamp |
| 112 | handgrip clamp lever |
| 114 | Clamp lever fulcrum |
| 116 | Clamp lever slot |
| 118 | Inner housing end wall |
| 120 | Outer housing end wall |
| 122 | inner housing handgrip end |
| 124 | Outer housing handgrip end |
| 126 | Outer housing handgrip channel at handgrip end of outer housing for receiving first spreader handgrip |
| 128 | Inner housing handgrip channel at handgrip end of inner housing for receiving second spreader handgrip |
| 130 | sliding end of inner housing |
| 132 | outer housing sliding end |
| 134 | inner housing proximal side wall |
| 136 | proximal side wall of outer housing |
| 138 | Inner housing distal side wall |
| 140 | distal side wall of outer housing |
| 142 | Exterior surface of outer housing front wall |
| 144 | Exterior surface of inner housing front wall |
| 146 | Exterior surface of inner housing proximal side wall |
| 148 | Proximal side wall interior surface, inner housing |
| 150 | proximal side wall exterior surface, outer housing |
| 152 | Interior surface of outer housing proximal side wall |
| 154 | Exterior surface of inner housing distal side wall |
| 156 | Distal side wall interior surface, inner housing |
| 158 | Distal side wall exterior surface, outer housing |
| 160 | Interior surface of the outer housing distal side wall |
| 162 | Interior void space of outer housing |
| 164 | Interior void space of inner housing |
| 166 | Force transducer clamp knob |
| 168 | Clamp knob threaded shaft |
| 170 | Radius of curvature of proximal side wall interior surface of outer housing |
| 172 | Radius of curvature of proximal side wall exterior surface of inner housing |
| 174 | handgrip clamp locked position |
| 176 | handgrip clamp unlocked position |
| 178 | Dimension of Gap for spreader handgrip (handgrip clamp unlocked) |
| 180 | Dimension of Gap for spreader handgrip (handgrip clamp locked) |
| 182 | Force transducer clamp assembly |

List of Reference Designators

| Reference Designator | Description |
| --- | --- |
| 184 | Force transducer |
| 186 | Displacement transducer |
| 188 | Outer housing front cover |
| 190 | Outer housing back cover |
| 192 | Inner housing front cover |
| 194 | Inner housing back cover |
| 196 | Interior surface, inner housing back cover |
| 198 | Interior surface, outer housing back cover |
| 200 | Force transducer clamp plate |
| 202 | Force transducer clamp block |
| 204 | Force transducer cantilever beam |
| 206 | Strain gauge |
| 208 | Displacement transducer stationary portion |
| 210 | Displacement transducer sliding armature |
| 212 | Link bar |
| 214 | First Rotatable coupling (link bar to outer housing back cover) |
| 216 | Rotatable coupling of link bar to displacement transducer sliding armature |
| 218 | Handgrip contact face; cylindrical surface of handle clamp lever |
| 220 | Center of curvature of cylindrical handgrip contact face |
| 222 | Radius of curvature of cylindrical surface |
| 224 | Rotational axis of clamp lever fulcrum 114 |
| 226 | Offset distance |
| 228 | Threaded aperture through outer housing front cover |
| 230 | Cantilever beam first end |
| 232 | Cantilever beam second end |
| 234 | Arcuate path traveled by first rotatable coupling 214 (link bar to outer housing back cover) |
| 236 | Center of rotation of 510 Handle rotational joint |
| 238 | Radial separation distance 214 to 236 |
| 240 | Angular displacement of link bar 212 about 214 rotatable coupling of link bar to outer housing back cover |
| 242 | Direction of Linear movement of 210 Displacement transducer sliding armature relative to 208 displacement transducer stationary portion |
| 244 | circuit board assembly |
| 246 | Transducer (xdcr) excitation |
| 248 | multiplexer |
| 250 | Acquisition controller |
| 252 | memory |
| 254 | Nonvolatile memory |
| 256 | Signal conditioning |
| 258 | Analog to Digital Converter (ADC) |
| 260 | Input/output (I/O) ports |
| 262 | Status indicators |
| 264 | Wired I/O |
| 266 | Wireless I/O |
| 268 | Electric storage battery |
| 270 | External data storage and/or display device |
| 272 | Separation distance between external surfaces of spreader jaws |
| 274 | Force measurement actuator |
| 276 | Aperture formed through outer housing sliding end 132 |
| 278 | Undeflected position of cantilever beam 204 |
| 280 | Deflected position of cantilever beam 204 |
| 282 | LED1 |
| 284 | LED2 |
| 286 | Mechanical force applied to 202 by relative movement of outer housing to inner housing |
| 288 | Magnitude of relative displacement of outer housing relative to inner housing |
| 500 | surgical spreader |
| 502 | First spreader handgrip |
| 504 | Second spreader handgrip |
| 506 | First spreader jaw |
| 508 | Second spreader jaw |
| 510 | handgrip rotational joint |
| 512 | fulcrum |
| 514 | First handgrip spring |
| 516 | Second handgrip spring |
| 518 | Spring fastener |
| 520 | Spreader handgrip locking mechanism |
| 522 | rotatable joint on handgrip post |
| 524 | handgrip post |
| 526 | Ratchet tooth |
| 528 | Tapered end of first spreader handgrip |
| 530 | Clamp bar |
| 532 | Interior jaw surface |
| 534 | Exterior jaw surface |
| 536 | Separation distance between exterior jaw surfaces |
| 538 | Threaded clamp rod |
| 540 | Handgrip locking knob |
| 542 | Threaded aperture in clamp knob |
| 544 | Aperture in spreader handgrip |
| 1000 | femur |
| 1002 | Surgically modified distal end of femur |
| 1004 | tibia |
| 1006 | Surgically modified proximal end of tibia |
| 1008 | collateral ligament (eg Lateral) |
| 1010 | collateral ligament (eg Medial) |
| 1012 | Gap between femur and tibia |
| 1014 | Distal end of femur prior to arthroplasty |
| 1016 | Cartilage at proximal end of tibia prior to arthroplasty |

The invention claimed is:

1. A measurement instrument, comprising:
a telescoping housing, comprising:
a first handgrip end;
a second handgrip end;
a first handgrip clamp positioned at said first handgrip end; and
a second handgrip clamp positioned at said second handgrip end;
a displacement transducer attached to said telescoping housing, said displacement transducer configured to measure a spatial displacement of said first handgrip end relative to said second handgrip end;
a force transducer attached to said telescoping housing, said force transducer configured to measure a mechanical force causing said spatial displacement; and
a circuit board assembly electrically connected to said displacement transducer and said force transducer, said circuit board assembly configured to receive a first electrical signal from said displacement transducer and a second electrical signal from said force transducer, convert said first electrical signal to a measured value of spatial displacement, convert said second electrical signal to a measured value of mechanical force, and transmit said measured value of spatial displacement and said measured value of mechanical force to another device.

2. The measurement instrument of claim 1, wherein said telescoping housing further comprises:
an outer housing, comprising:
said first handgrip end;
an outer housing sliding end opposite said first handgrip end;
an outer housing proximal side wall;
an outer housing distal side wall;

an outer housing end wall extending from said outer housing proximal side wall to said outer housing distal side wall; and said outer housing formed with an outer housing handgrip channel extending through said first handgrip end to said outer housing end wall, through said outer housing proximal side wall, and through said outer housing distal side wall; and an inner housing, comprising:

said second handgrip end;

an inner housing sliding end opposite said second handgrip end;

an inner housing proximal side wall;

an inner housing distal side wall;

an inner housing end wall extending from said inner housing proximal side wall to said inner housing distal side wall;

said inner housing formed with an inner housing handgrip channel extending through said second handgrip end to said inner housing end wall, through said inner housing proximal side wall, and through said inner housing distal side wall; and said inner housing slidably engaged with said outer housing with said inner housing sliding end passing through an aperture formed through said outer housing sliding end.

3. The measurement instrument of claim 2, wherein said first handgrip clamp comprises:

a handgrip clamp lever comprising:

a handgrip contact face at an end of said handgrip clamp lever; and a clamp lever fulcrum extending outward from said handgrip clamp lever, said claim lever fulcrum having a rotational axis offset from a center of curvature of said handgrip contact face;

a clamp lever slot formed through said outer housing, said clamp lever slot extending into said outer housing handgrip channel and through said first handgrip end, with said clamp lever slot sized to admit said clamp lever fulcrum; and said handgrip clamp lever rotatably coupled to said outer housing with said clamp lever fulcrum removably engaged in said clamp lever slot.

4. The measurement instrument of claim 2, wherein said second handgrip clamp comprises:

a handgrip clamp lever comprising:

a handgrip contact face at an end of said handgrip clamp lever; and a clamp lever fulcrum extending outward from said handgrip clamp lever, said claim lever fulcrum having a rotational axis offset from a center of curvature of said handgrip contact face;

a clamp lever slot formed through said inner housing, said clamp lever slot extending into said inner housing handgrip channel and through said second handgrip end, with said clamp lever slot sized to admit said clamp lever fulcrum; and said handgrip clamp lever rotatably coupled to said inner housing with said clamp lever fulcrum removably engaged in said clamp lever slot.

5. The measurement instrument of claim 2, wherein said force transducer comprises:

a clamp block slidably engaged with said outer housing;

a cantilever beam having a first end affixed to said clamp block and a second end affixed to said inner housing; and a strain gauge affixed to said cantilever beam, said strain gauge configured to measure a mechanical force causing a deflection of said first end of said cantilever beam relative to said second end of said cantilever beam.

6. The measurement instrument of claim 5, further comprising a force measurement actuator comprising:

a force transducer clamp knob having a threaded shaft engaged with a threaded aperture formed in said outer housing; and a force transducer clamp plate positioned for contact with said threaded shaft and for sliding contact with said clamp block, wherein said clamp block is immobilized against said outer enclosure by sufficient advancement of said threaded shaft against said force transducer clamp plate, thereby enabling a measurement of mechanical force causing a displacement of said outer housing relative to said inner housing.

7. The measurement instrument of claim 2, wherein said displacement transducer comprises:

a stationary portion fixed to said inner housing; and a sliding armature slidably engaged with said stationary portion and rotatably coupled to said outer housing.

8. The measurement instrument of claim 7, further comprising:

a first rotatable coupling attached to said outer housing;

a link bar rotatably coupled to said outer housing by said first rotatable coupling;

a second rotatable coupling attached to said sliding armature; and said link bar rotatably coupled to said sliding armature by said second rotatable coupling.

9. The measurement instrument of claim 1, said circuit board assembly further comprising:

a transducer excitation circuit connected for signal communication with said force transducer and said displacement transducer;

a signal conditioning circuit connected for signal communication with said force transducer and said displacement transducer;

an analog to digital converter connected for signal communication with said signal conditioning circuit; and an acquisition controller connected for signal communication with said analog to digital converter and a memory.

10. The measurement instrument of claim 9, further comprising a multiplexer interposed in electrical connections between said force transducer, said displacement transducer, and said signal conditioning circuit.

11. The measurement instrument of claim 9, further comprising a multiplexer interposed in electrical connections between said force transducer, said displacement transducer, and said transducer excitation circuit.

12. The measurement instrument of claim 9, wherein said circuit board assembly further comprises a wireless communications device connected for signal communication with said acquisition controller and configured for wireless signal communication with another measurement instrument.

13. The measurement instrument of claim 12, wherein said acquisition controller is configured to transmit said measured value of displacement and said measured value of force to another of said measurement instrument.

14. The measurement instrument of claim 9, wherein said acquisition controller is configured to:

store said measured value of force in said memory;

store in said memory a second measured value of force received from another of said measurement instrument;

determine a magnitude of difference between said measured value of force and said second measured value of force;

activate a first status indicator when said magnitude of difference is greater than a stored threshold value; and activate a second status indicator when said magnitude of difference is less than or equal to said stored threshold value.

\* \* \* \* \*